US010139348B2

(12) United States Patent
Tajima

(10) Patent No.: US 10,139,348 B2
(45) Date of Patent: Nov. 27, 2018

(54) LIGHTGUIDE AGGREGATE INSPECTION DEVICE AND INSPECTION METHOD OF THE SAME

(71) Applicant: Universal Bio Research Co., Ltd., Matsudo-shi, Chiba (JP)

(72) Inventor: Hideji Tajima, Matsudo (JP)

(73) Assignee: UNIVERSAL BIO RESEARCH CO., LTD., Matsudo-Shi, Chiba (JP)

( * ) Notice: Subject to any disclaimer, the term of this patent is extended or adjusted under 35 U.S.C. 154(b) by 239 days.

(21) Appl. No.: 15/127,119

(22) PCT Filed: Mar. 20, 2015

(86) PCT No.: PCT/JP2015/058467

§ 371 (c)(1),
(2) Date: Sep. 19, 2016

(87) PCT Pub. No.: WO2015/141828

PCT Pub. Date: Sep. 24, 2015

(65) Prior Publication Data

US 2018/0172597 A1 Jun. 21, 2018

(30) Foreign Application Priority Data

Mar. 20, 2014 (JP) ................................ 2014-059164

(51) Int. Cl.
*G01J 3/46* (2006.01)
*G01N 21/78* (2006.01)
(Continued)

(52) U.S. Cl.
CPC ......... *G01N 21/78* (2013.01); *G01N 21/0332* (2013.01); *G01N 21/64* (2013.01);
(Continued)

(58) Field of Classification Search
CPC ........ G01N 21/78; G01N 21/76; G01N 21/64; G01N 21/65; G01N 35/10; H01L 31/167; F21V 8/00; G01J 3/46; G01J 3/02
See application file for complete search history.

(56) References Cited

U.S. PATENT DOCUMENTS 6,123,903 A 9/2000 Tajima
7,023,544 B2 4/2006 Cunningham et al.
(Continued)

FOREIGN PATENT DOCUMENTS

JP 7110330 A 4/1995
JP 2003294630 A 10/2003
JP 200577264 A 3/2005

OTHER PUBLICATIONS

English translation of International Search Report issued by the Japan Patent Office regarding International Application No. PCT/JP2015/058467 dated Jun. 16, 2015, 2 pages.
(Continued)

*Primary Examiner* — Abdullahi Nur
(74) *Attorney, Agent, or Firm* — Haynes and Boone, LLP

(57) ABSTRACT

A lightguide aggregate inspection device includes a reaction spot array including multiple reaction spot array elements having at least one reaction spot, a light-receiving element array having a light-receiving surface provided with multiple light-receiving regions each having at least one light-receiving element corresponding to each of the reaction spot array elements, and receiving light obtained based on an optical state resulting from reaction in each of the reaction spots, multiple lightguide paths provided to correspond to the reaction spot array elements, and each having a measurement end provided close to or in contact with, or to be movable close to or into contact with 1 reaction spot, and a connection end provided close to or in contact with the light-receiving region, and a digital data conversion unit configured to convert image region data obtained from the light-receiving elements corresponding to the light-receiving regions, into digital data.

16 Claims, 10 Drawing Sheets

(51) Int. Cl.

| | |
|---|---|
| ***G01N 21/03*** | (2006.01) |
| ***G01N 35/00*** | (2006.01) |
| ***G01N 21/64*** | (2006.01) |
| ***G01N 21/76*** | (2006.01) |
| ***F21V 8/00*** | (2006.01) |
| ***H01L 31/167*** | (2006.01) |
| *G01N 35/10* | (2006.01) |

(52) U.S. Cl.

CPC ......... *G01N 21/76* (2013.01); *G01N 35/0098* (2013.01); *G01N 35/10* (2013.01); *G02B 6/0036* (2013.01); *H01L 31/167* (2013.01); *G01N 2035/1062* (2013.01); *G01N 2201/0833* (2013.01)

(56) References Cited

U.S. PATENT DOCUMENTS

| | | | | |
|---|---|---|---|---|
| 2002/0068698 | A1 | 6/2002 | Meyers et al. | |
| 2004/0114890 | A1 | 6/2004 | Tajima | |
| 2009/0088336 | A1 | 4/2009 | Burd et al. | |
| 2009/0161100 | A1* | 6/2009 | Minot .................... | G02B 21/34 356/244 |
| 2010/0285996 | A1 | 11/2010 | Tajima | |
| 2011/0212537 | A1 | 9/2011 | Rissin et al. | |
| 2014/0134620 | A1 | 5/2014 | Tajima | |
| 2015/0210437 | A1 | 7/2015 | Tajima | |

OTHER PUBLICATIONS

Written Opinion issued by the Japan Patent Office regarding International Application No. PCT/JP2015/058467 dated Jun. 16, 2015, 5 pages.

* cited by examiner

【Fig. 1】
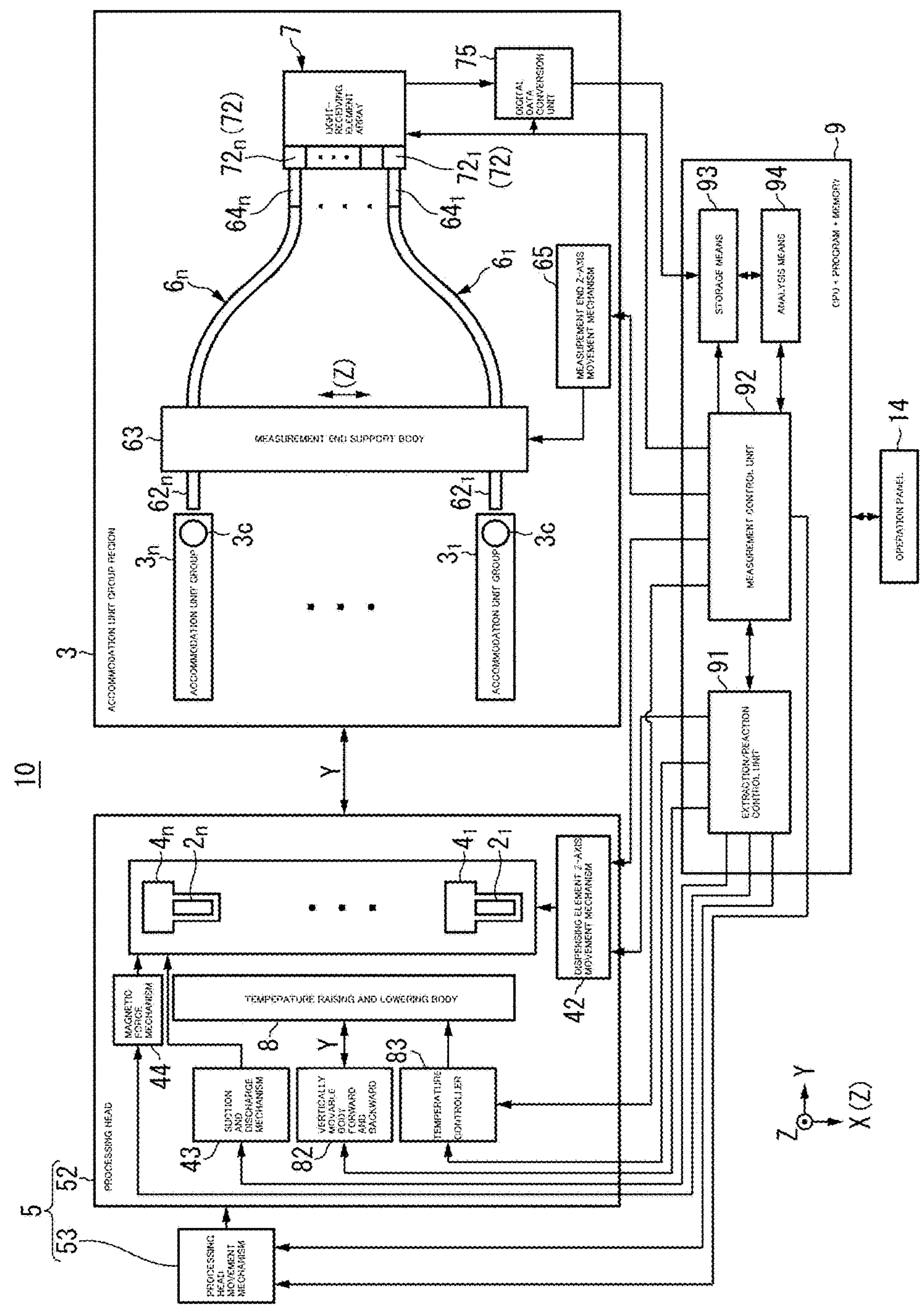

【Fig. 2】
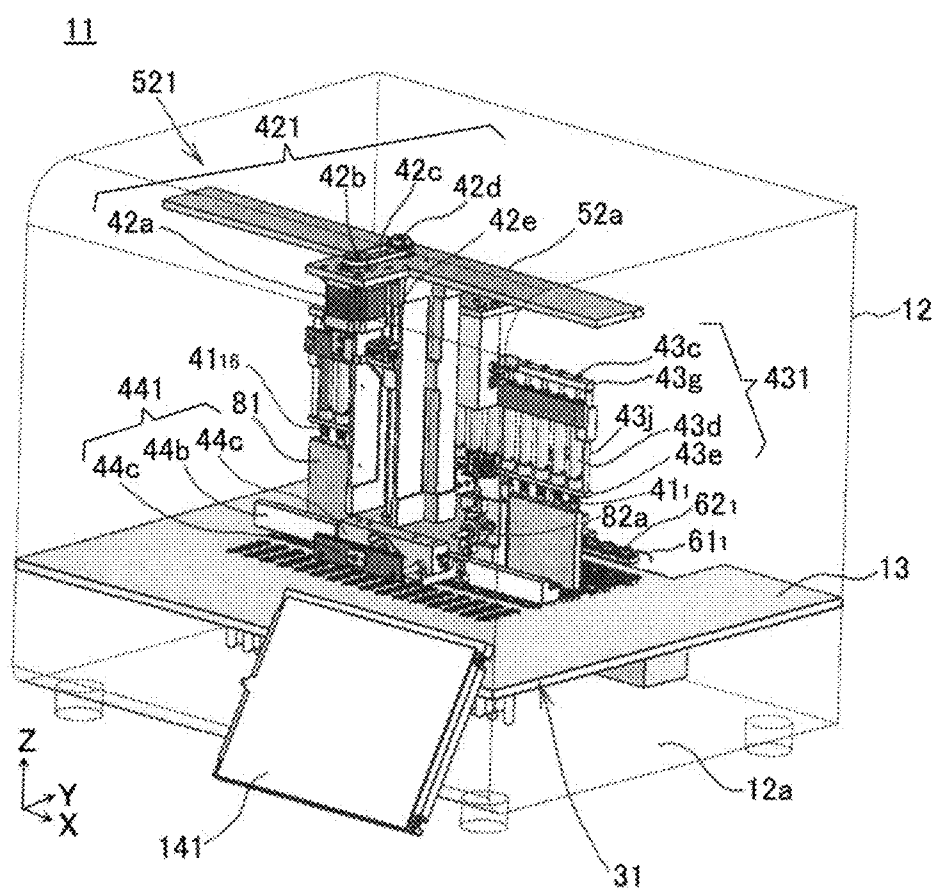

【Fig. 3】
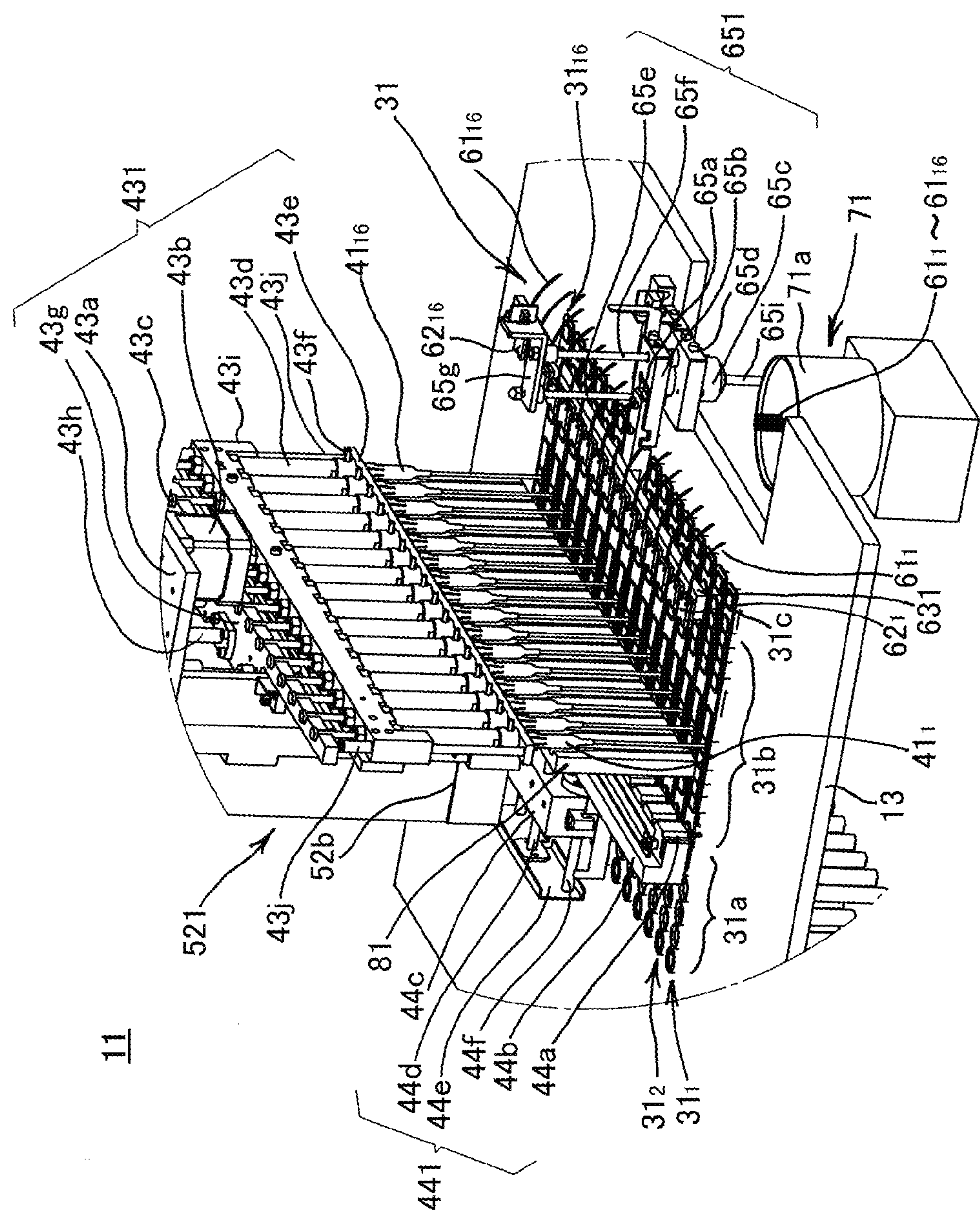

【Fig. 4】
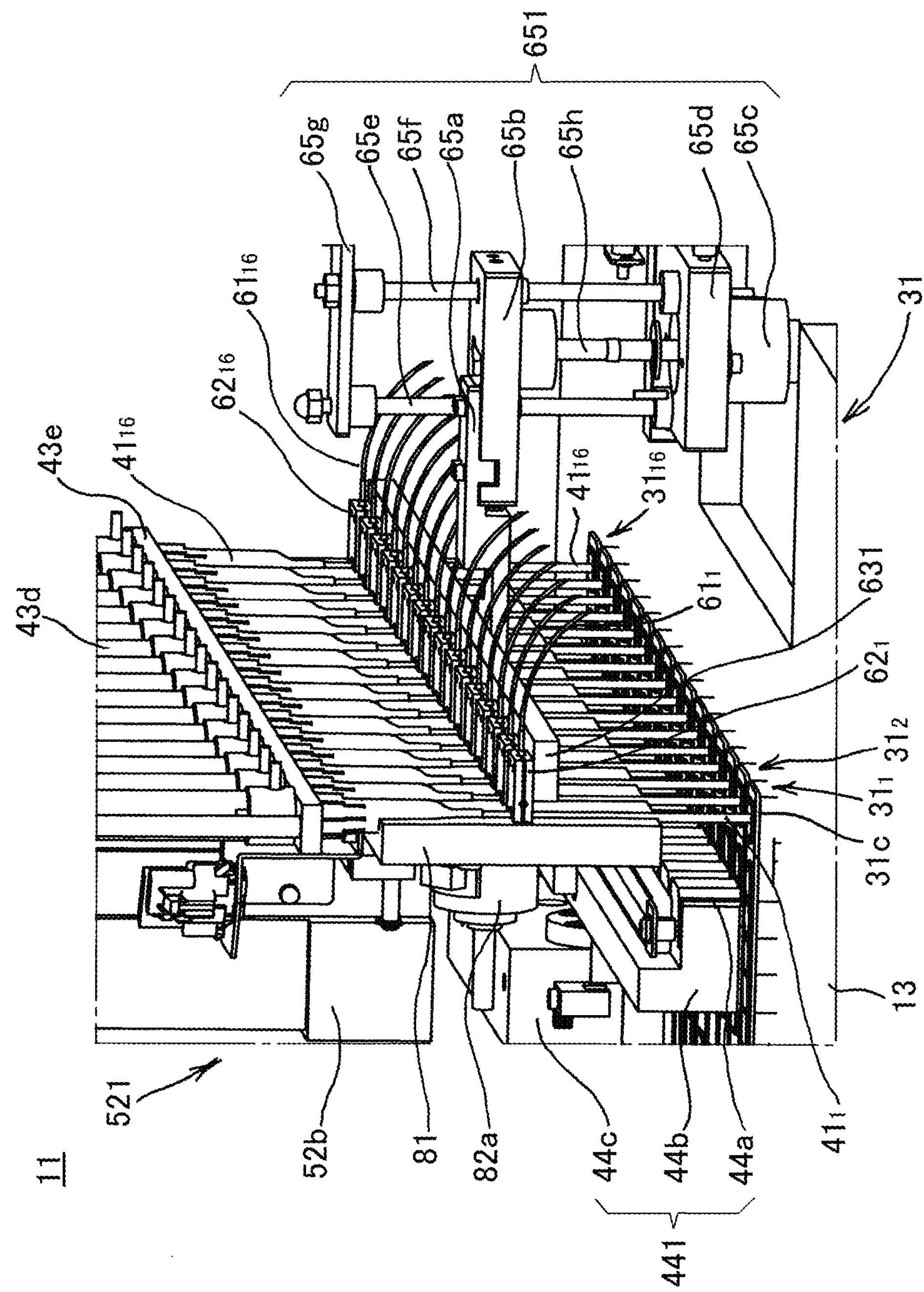

【Fig. 5】
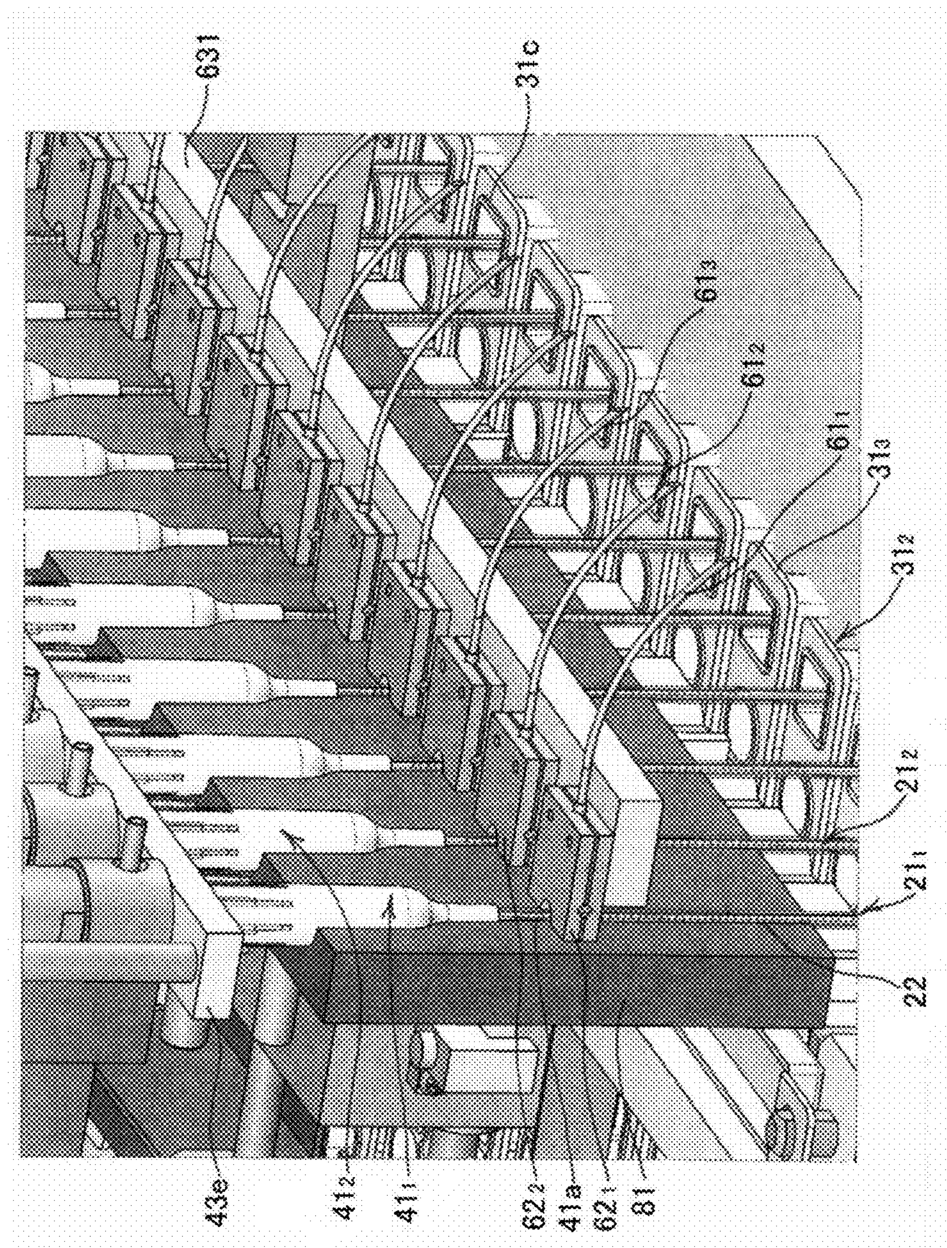

【Fig. 6】
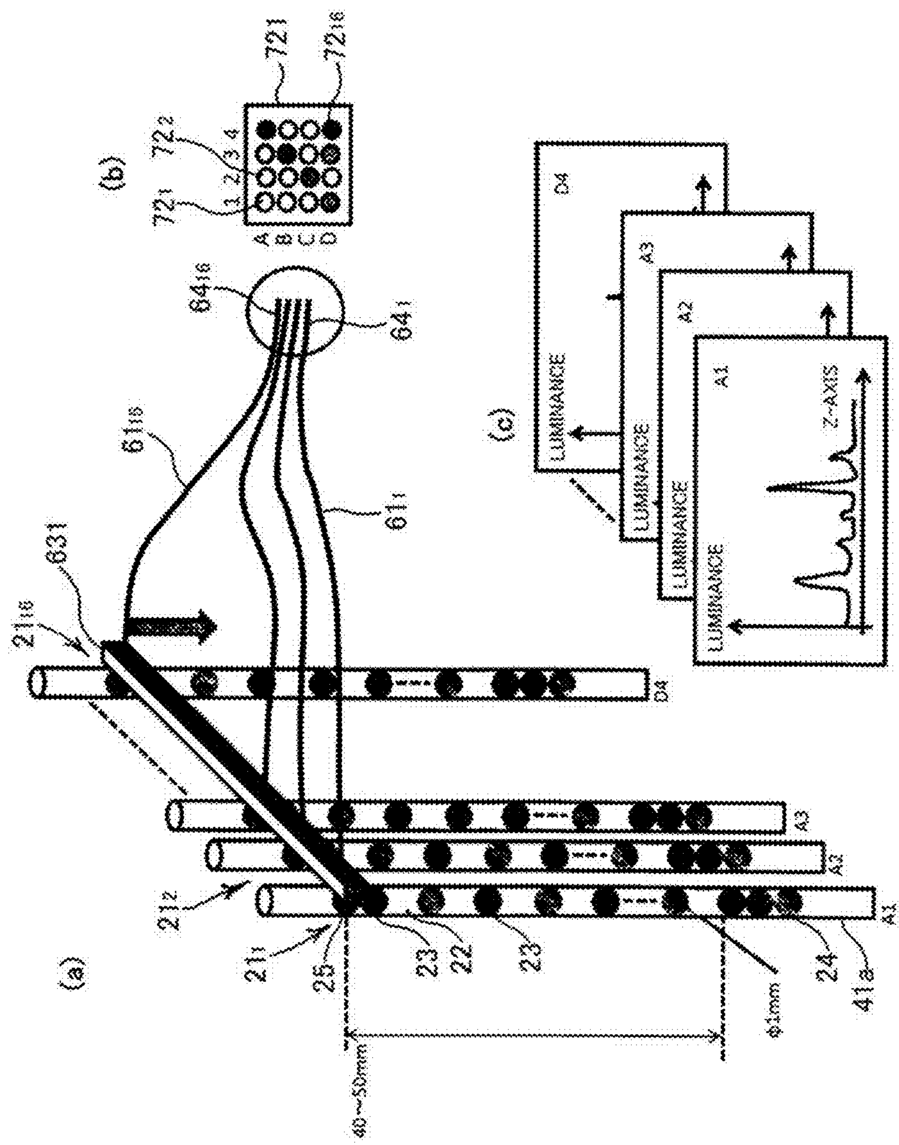

【Fig. 7】
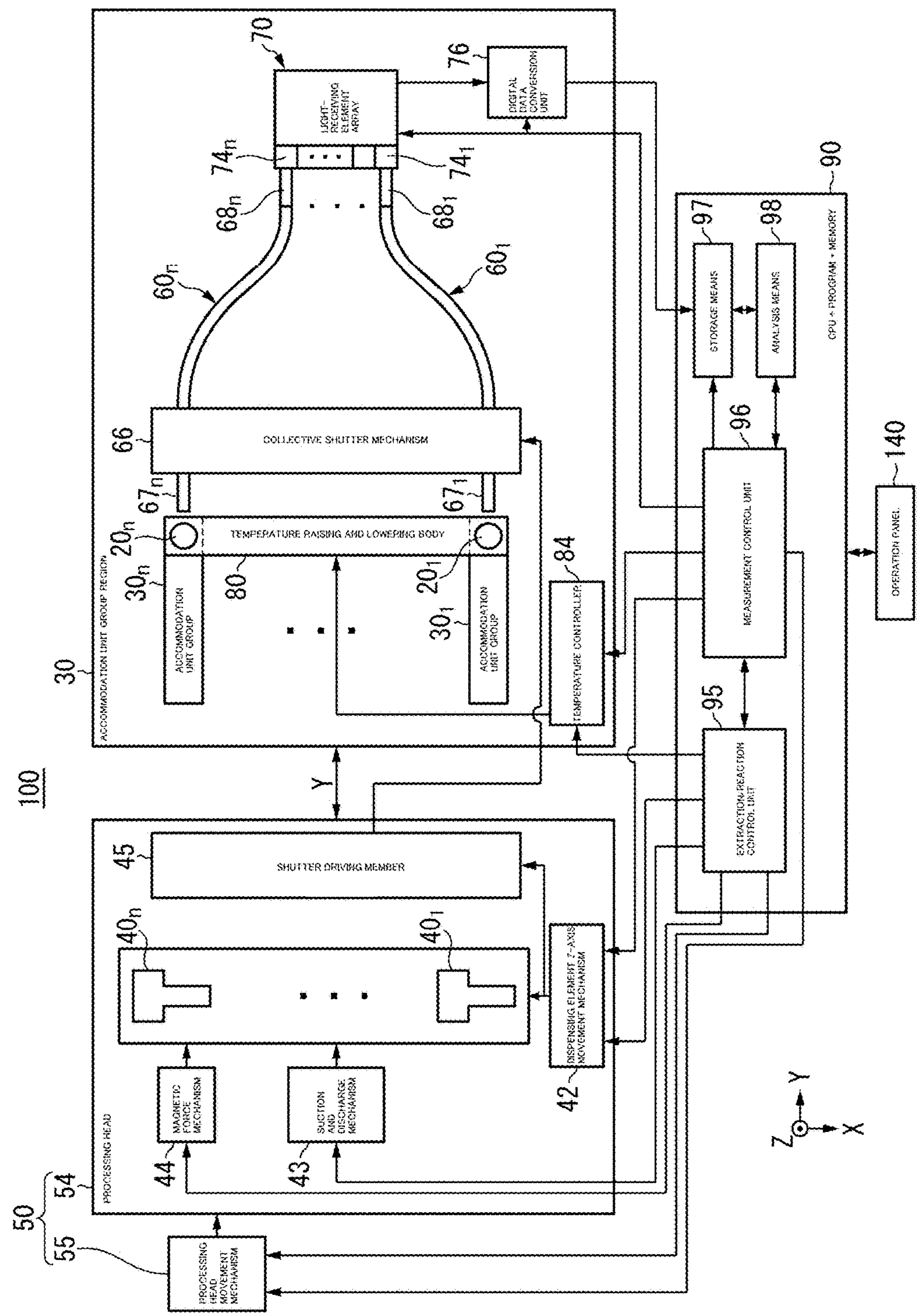

【Fig. 8】
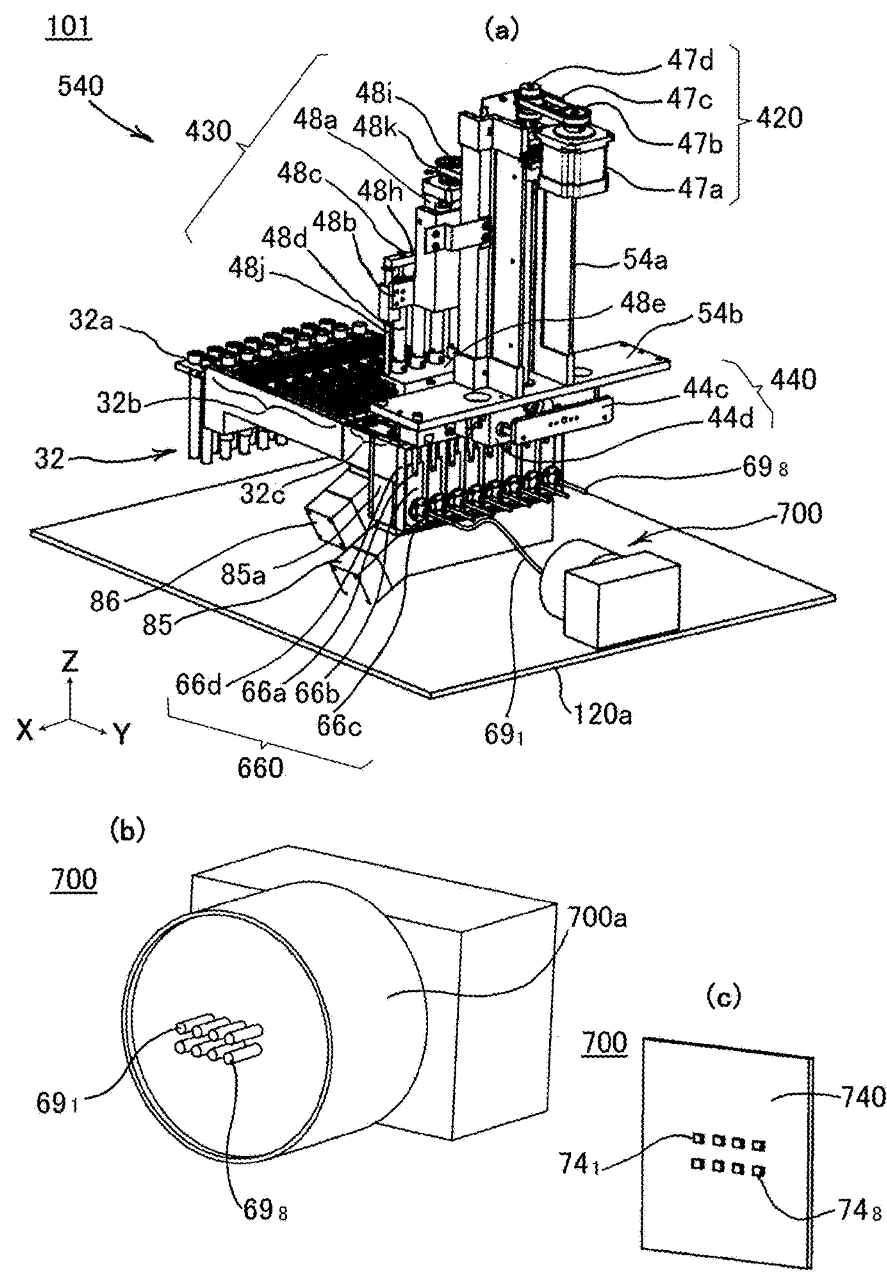

【Fig. 9】
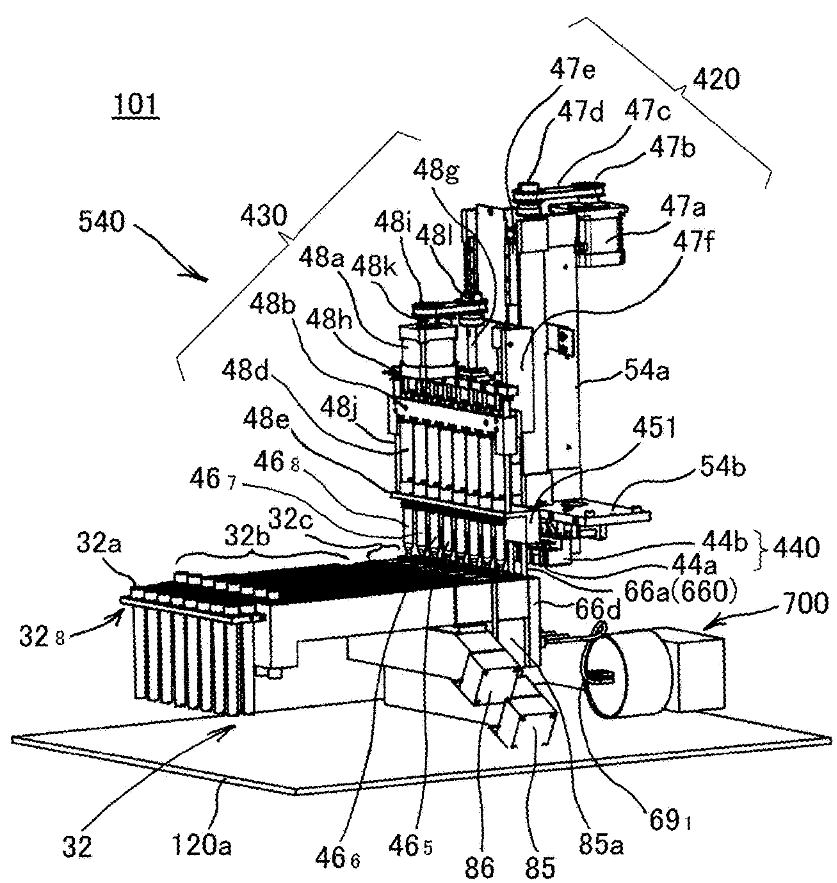

【Fig. 10】
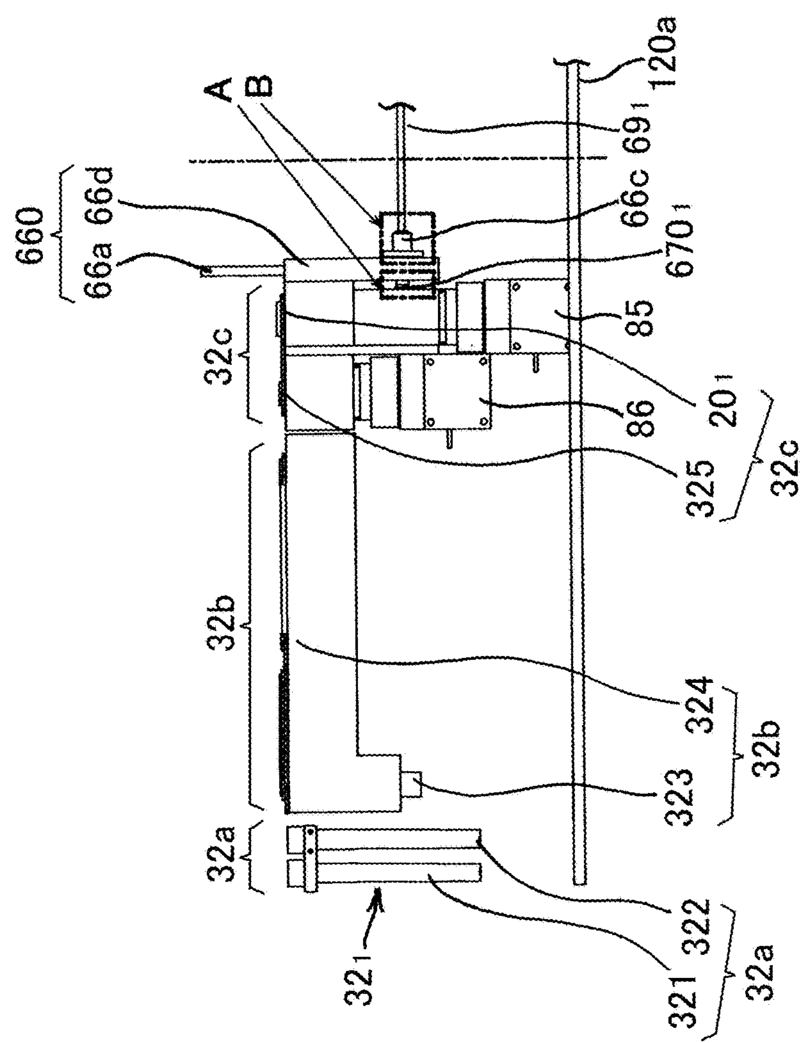

LIGHTGUIDE AGGREGATE INSPECTION DEVICE AND INSPECTION METHOD OF THE SAME

CROSS REFERENCE

This application is a United States national phase application of co-pending international patent application number PCT/JP2015/058467, filed Mar. 20, 2015, which claims priority to Japanese patent application number 2014-059164, filed Mar. 20, 2014, the disclosures of which are incorporated herein by reference.

TECHNICAL FIELD

The present invention relates to a lightguide aggregate inspection device that uses a lightguide path such as an optical fiber, and an inspection method of the same.

BACKGROUND ART

In recent years, the inspection of a target biological substance has been performed in the following manner. First, a target biological substance to be inspected is extracted from a specimen collected from a subject or the like, and the extracted target biological substance is labeled using a fluorescent substance or a chemiluminescent substance. Then, solution containing the target biological substance is brought into contact with a carrier such as a DNA chip or a string-like probe array that planarly or one-dimensionally fixes multiple types of inspection substances (probes) having a prescribed relation with the target biological substance, at predefined multiple different positions identifiable from the outside. Alternatively, the solution is accommodated into a well of a microplate that accommodates or fixes the inspection substance. Reaction is thereby caused, and the inspection of the target biological substance is performed based on the presence or absence of fluorescence or chemiluminescence in each position on the carrier or in each well.

The measurement of fluorescence or chemiluminescence has been normally performed by scanning the carrier from each fixed position on the carrier or from the microplate using 1 or multiple optical fibers, or by guiding light from each fixed position on the carrier to a light-receiving element or an imaging element (Patent Literatures 1 and 2).

In addition, there has been a device that performs measurement in the following manner (Patent Literature 3). In place of the carrier, 1 or multiple types of target biological substances labeled using a chemiluminescent substance are accommodated into 1 container. By injecting trigger solution, light is guided to 1 PMT via an optical fiber or the like that is provided in the container for measuring the presence or absence of luminescence thereof. The measurement is thereby performed.

CITATION LIST

Patent Literature

Patent Literature 1: WO 02/063300 A1
Patent Literature 2: JP 2003-294630 A
Patent Literature 3: JP 3822637 B1

SUMMARY OF INVENTION

Technical Problem

Nevertheless, because light is guided using a large number of optical fibers each having one end fixed to each fixed position on a DNA chip or a carrier having a string shape or the like, or to each well, conventional techniques have the following problems. If the number of fixed positions or wells used in the inspection increases, the number of expensive PMTs increases, or the number of optical fibers increases. In addition, in a case in which measurement is performed by performing scanning, light needs to be guided to PMTs while sequentially performing switching. The processing accordingly requires time. In addition, a switching mechanism is required. For various reasons, a device may increase in scale or cost.

In particular, if measurement is to be concurrently performed in a carrier or a well having a large number of fixed positions, processing needs to be concurrently performed from a stage of preprocessing of reaction processing with the carrier or the like, such as extraction preprocessing of each sample and labeling preprocessing, even before reaching a measurement stage. This causes problems in that a processing procedure and a device structure may be complicated.

Thus, the present invention has been devised for solving the above-described problems, and the first purpose of the present invention is to provide a lightguide aggregate inspection device that can quickly and temporally-efficiently perform inspection by concurrently performing processing and measurement in a case in which a large number of or multiple probe arrays and reaction containers are provided, and an inspection method of the same. The second purpose is to provide a lightguide aggregate inspection device that can consistently and concurrently perform processing from reaction between a target substance to be inspected, and a probe array or various types of solution, to measurement, and an inspection method of the same. The third purpose is to provide a lightguide aggregate inspection device that has a compact device structure by receiving light in an aggregated manner using a lightguide path, in a case in which a large number of or multiple probe arrays and reaction containers are provided, and can spatially-efficiently perform inspection, and an inspection method of the same.

Solution to Problem

The first invention is a lightguide aggregate inspection device including a reaction spot array including multiple reaction spot array elements having at least one reaction spot in which reaction related to inspection is performed, and which is provided at a predefined different position identifiable from an outside, a light-receiving element array having a light-receiving surface provided with multiple light-receiving regions each having at least one light-receiving element corresponding to each of the reaction spot array elements, and receiving light obtained based on an optical state resulting from reaction in each of the reaction spots, multiple lightguide paths provided to correspond to the reaction spot array elements, and each having a measurement end provided to be close to or in contact with, or to be movable close to or into contact with 1 of the reaction spots, and a connection end provided to be close to or in contact with the light-receiving region, a digital data conversion unit configured to convert, at a prescribed period, image region data obtained from the light-receiving elements corresponding to the light-receiving regions, to obtain digital data for each of the light-receiving regions, and a storage means configured to sequentially store the digital data.

Herein, the “reaction spot” refers to a location where reaction is performed, and is, for example, a liquid accommodation unit that accommodates or can accommodate various types of inspection solution used in reaction related to inspection, or a fixed position on an inspection carrier where various types of inspection substances used in reaction related to inspection are fixed. In addition, the "inspection carrier" refers to a carrier fixed at each fixed position where multiple types of inspection substances having prescribed chemical structures are arranged at a prescribed interval, and associated with each chemical structure and a corresponding fixed position. The "reaction spot array element" refers to a region obtained by dividing the reaction spot array in such a manner that each includes at least one reaction spot, and includes a case of being integrally formed, in addition to a case of being separately formed. For example, the reaction spot array element includes a case of being 1 liquid accommodation unit (container), and a case of being separately formed inspection carriers. The "contact" includes close contact, adhesion, or connection. The "liquid accommodation unit" also includes a reaction container that can control temperature.

In a case in which the reaction spot is a liquid accommodation unit, the reaction spot array is, for example, a microplate in which wells serving as multiple liquid accommodation units are two-dimensionally arrayed, or a one-dimensionally arrayed cartridge container. Alternatively, the reaction spot array includes a case in which the microplates are stacked at an interval also in a height direction to be three-dimensionally arrayed. The reaction spot array element can be, for example, 1 or more liquid accommodation units, 1 or more cartridge containers, or 1 or more microplates.

In a case in which reaction spots are on an inspection carrier, the reaction spot array can be, for example, a bar-like, needle-like, reed-shaped, ribbon-like, threadlike, or tape-like carrier in which the fixed positions are one-dimensionally arrayed, or two-dimensionally arrayed plate-like, bar-like, reed-shaped, tape-like, or ribbon-like carriers. Furthermore, in a case in which the inspection carrier has a three-dimensional shape, and reaction spots are fixed on the surface of the three-dimensional shape, the reaction spots can be said as being three-dimensionally arrayed. In addition, in a case in which an inspection carrier is formed of multiple particulate carriers (particles), each particle corresponds to a fixed position. In this case, the reaction spot array element can be, for example, 1 or more inspection carriers.

Examples of the inspection substance include a genetic substance such as nucleic acid or a biological substance such as a protein substance, sugar, sugar chain, and peptide that has a binding property with respect to a target biological substance to be inspected, or solution thereof. In the inspection using these inspection substances, asides from these, there is a substance or solution related to chemiluminescence, for example, as a substance or solution related to the inspection. For example, as substances used for chemiluminescence reaction, there are 1) luminol or isoluminol derivative/hydrogen peroxide, 2) acridinium ester derivative/hydrogen peroxide, and 3) acridinium acyl sulfonamide derivative, and the like. In this case, there are a CLIA method and a CLEIA method. In the CLIA method, chemiluminescence detection is performed using, as trigger reagent, alkaline hydrogen peroxide in acridinium derivative or hydrogen peroxide and micro-peroxidase (m-POD) in isoluminol derivative for direct labeling. In the CLEIA method, after an enzyme is labeled, chemiluminescence detection is performed for measuring the activity of a labeling enzyme. Because the enzyme is used for labeling, a method for not deactivating an enzyme activity in B/F separation is required. For example, in a case in which horseradish peroxidase is used as an enzyme, luminol/hydrogen peroxide is used as a substrate for detection. In addition, in a case in which glucose oxidase is used as an enzyme, glucose/TCPO/ANS is used as a substrate. For measuring glucose-6-phosphate dehydrogenase (G6PDH), if NADP is used in coenzyme with glucose-6-phosphate serving as a substrate, NADPH is generated by enzyme reaction. Thus, G6PDH can be detected through chemiluminescence reaction of the NADPH.

The "light-receiving element array" refers to a sensor having a light-receiving surface on which light-receiving portions of multiple or a large number of light-receiving elements are arrayed linearly or planarly, for example. Examples of highly-sensitive light-receiving elements include an avalanche photodiode (APD) array manufactured by Hamamatsu Photonics. Special cases in which density of light-receiving element array is high include, for example, an "imaging sensor" such as a CCD image sensor and a CMOS image sensor. For example, such cases include BITRAN BU-50LM (ICX415AL) with 6.4×4.8 mm and 772×580 pixels. By processing image region data (an analog signal) obtained by a light-receiving element belonging to each light-receiving region of a light-receiving element array, a corresponding digital signal is obtained for each light-receiving region. These are formed by an integrated circuit (IC). The "image region data" refers to an aggregate of data obtained from light-receiving elements corresponding to the light-receiving regions, considering an array of the light-receiving elements, and corresponds to pixel data in a case in which there is only 1 light-receiving element in the light-receiving region, or image data in a case in which there are multiple or a large number of light-receiving elements such as the above-described number (772×580 pixels) approximately.

The "light-receiving element" refers to an electron element utilizing a photoelectric effect, and is a photodiode, phototransistor, or the like. Furthermore, the "light-receiving element" includes a photon counting sensor having a multiplying effect such as the APD, and the like. The "prescribed period" refers to a time in which sufficient level of light required for inspection can be received for each reaction spot, and is defined according to a light measurement mode including 1 or 2 or more elements selected from the group consisting of the detail of an optical state to be measured, the type of luminescence (e.g., the type of fluorescent substance, the type of chemiluminescent substance), a reagent used for luminescence (including the type of reagent and the amount of reagent), the number of light-receiving times for 1 reaction spot, the mode of luminescence (e.g., instantaneous luminescence, plateau-like luminescence, the life of luminescence, stable light receptible time, etc.), a mode of movement from a light-receiving position to the next light-receiving position (in a case in which the measurement end is scanned between reaction spots of the reaction spot array element, intermittent operation, continuous operation, scanning speed, movement distance, movement time, stop time, movement route, etc.), the size of reaction spots, the arrangement, the number, or the like of reaction spots, the size of a lightguide portion, a distance between reaction spots, an exposure time, a reaction time in the reaction spots, and the like. In addition, data transfer or data readout time (in the case of using CCD) is considered in some cases. For example, in a case in which the amount of light is large as in the case of fluorescence, a prescribed period is short, and the prescribed period is set to be longer as the amount of light becomes smaller. For example, in the case of measuring an end point of chemiluminescence, the prescribed period is, for example, about 1 second to 10 seconds, and is shorter in a case in which the amount of light is large as in fluorescence or the like, and is about 0.01 seconds to 0.1 seconds, for example. In a case in which the measurement end is scanned between reaction spots, and in the case of plateau-like chemiluminescence, if a light measurement mode including a stable light receptible time (T) in which the plateau is maintained, the number of reaction spots (m), the number of light-receiving times (r) for each reaction spot, and an intermittent operation is selected, a prescribed period is set to $T/(m \cdot r)$, and this period includes the time of movement from a light-receiving position to the next light-receiving position, and a time for the digital data conversion at the light-receiving position. In addition, in the case of a CCD image sensor, for example, the "digital data conversion unit" includes a shift register that can perform gate control, an amplifier, and an AD converter. In the case of a photon counting sensor using a PMT photon counting sensor that generates photons in the number set according to the intensity or luminance of light received by the light-receiving element, and a semiconductor, the "digital data conversion unit" includes a pulse counter that can perform gate control and serves as a photon counter, and is formed by an IC circuit similarly to the light-receiving element array. According to an instruction from a measurement control unit to be described later, these operate in the prescribed period obtained based on the light measurement mode.

Generated digital data is stored into a storage means of a semiconductor storage element such as a DRAM. Then, through calculation processing, a temporal change of luminance of an optical state is obtained based on digital data obtained by converting image region data of 1 or 2 or more light-receiving elements belonging to each light-receiving region corresponding to each of the reaction spot array elements, at a prescribed period, to be analyzed. The "prescribed period" is set based on an instruction signal such as a pulse signal output based on a measurement control unit provided in an information processing unit including a driving unit or a CPU, a program, and a memory that generate a pulse signal at the period, for example.

It is defined that "at least one light-receiving element is included" because, in a case in which a light-receiving element is highly-sensitive, a monochromatic optical state can be detected by at least one light-receiving element. In addition, in a case in which at least 3 light-receiving elements are included, color light receiving can be performed based on light received through a color filter (RGB) for each light-receiving element. In addition, the size, shape, or range of each of the light-receiving regions depends on the size or sensitivity of the light-receiving element, the size or shape of a connection end of the lightguide path, an interval between connection ends, an interval between the connection end and a light-receiving surface, the shape of the connection end, or the mode of an optical state.

The "digital data" is data representing, for example, a numerical value processable by an information processing device such as a CPU. In a case in which the number of light-receiving elements corresponding to each light-receiving region is large, for example, the data can be stored into a storage means by compression, thinning out of image region data, or the like. The storage means is a memory recording data, and is a semiconductor memory, hard disk, CD, DVD, SSD, blu-ray disc, or the like.

The "lightguide path" includes, for example, a cavity, an optical element such as a lens, an optical fiber, and the like. The optical fiber is, for example, a plastic optical fiber that can handle visible light with an outer diameter of 500 μm. The optical fiber includes an optical fiber bundle bundling multiple optical fibers.

The "optical state" includes luminescence caused by fluorescence or chemiluminescence, colored, light variation, color change, and the like. In a case in which an optical state is "fluorescence", it is preferable to include a second lightguide path, which is a lightguide path for emitting excitation light onto the reaction spot, and which has an emission end that is provided to be close to or in contact with, or can move close to or into contact with 1 of the reaction spots of the reaction spot array, and a connection end provided to be close to or in contact with a light source surface of a light source of the excitation light. In addition, in a case in which an optical state is "colored", it is preferable to include a third lightguide path, which is a waveguide path for emitting reference light onto each of the reaction spots, and which has an emission end that is provided to be close to or in contact with, or can move close to or into contact with 1 of the reaction spots of the reaction spot array, and a connection end provided to be close to or in contact with a light source surface of a light source of the reference light. In these cases, the measurement end is preferably bundled with its leading edge aligned with the emission end to be treated as a measurement end.

The "light-receiving surface" is a surface formed by arraying light-receiving portions of the light-receiving elements, and is dense in the case of an imaging sensor, or rough in the case of an ADP array. In addition, stored digital data is read out by an analysis means of an information processing unit including a CPU and the like, to be calculated and analyzed. The inspection of a target biological substance is thereby performed.

The second invention is a lightguide aggregate inspection device, in which the reaction spot array element includes 2 or more reaction spots, and which further includes a measurement end support body configured to support a multiple of the measurement ends in an array set according to an array of the reaction spot array elements, and a measurement end movement mechanism configured to make the measurement end support body relatively-movable with respect to the reaction spot array, and to thereby enable the measurement ends to concurrently move close to or into contact with the reaction spots corresponding to the respective reaction spot array elements.

Herein, the "measurement end movement mechanism" can relatively move the measurement end support body with respect to the spot array. Thus, there can be a case of moving the measurement end support body, a case of moving the reaction spot array, and a case of combining these cases. In addition, there is included a case of moving the measurement end support body in such a manner as to be sequentially scanned between the reaction spots by relatively moving the measurement end support body with respect to the reaction spot array to move close to or into contact with a corresponding reaction spot, and then further move close to or into contact with the next corresponding reaction spot within each reaction spot array element. In this case, the arrays of reaction spots between the reaction spot array elements do not necessarily have to be congruent. For example, examples of such cases include a case in which the array of reaction spots in another reaction spot array element is similar (a case in which an array pattern is the same, but the magnification ratio of the size is not 1, and a case in which the magnification ratio is 1 correspond to "congruent".), a case of a reaction spot array element partially having portions to which reaction spots are not set at corresponding positions in the reaction spot array element, and the like. For example, in the case of reaction spot array elements including multiple particulate carriers, in a case in which the number of particles and the sizes and shapes of particles are the same, and the modes of the arrays (e.g., linearly arraying in a line without creating gaps) are the same, the arrays are congruent. For example, in a case in which only the sizes of particles do not correspond to the magnification ratio of 1, the arrays are similar. The "prescribed period" is preferably defined according to a time of movement between reaction spots or the like that is defined according to a speed of movement of the measurement ends that is caused by the measurement end movement mechanism that can concurrently move the measurement ends close to or into contact with reaction spots in the respective reaction spot array elements, and a distance between reaction spots. Thus, the image region data is preferably converted into digital data in synchronization with the measurement end movement mechanism. In addition, the material of the particle is ceramics, resin, or the like, for example.

The third invention is a lightguide aggregate inspection device, in which, in each of the reaction spot array elements, 2 or more reaction spots are arrayed so as to be congruent to each other, the reaction spot array elements are arrayed so as to have translation symmetry to each other, and the measurement end support body is arranged so as to enable the measurement ends provided to correspond to the respective reaction spot array elements, to concurrently and sequentially move close to or into contact with 2 or more of the reaction spots corresponding between the reaction spot array elements.

Here, because "2 or more reaction spots are arrayed so as to be congruent to each other", the shape of the carrier of each reaction spot array element itself is not limited. For example, in a case in which the reaction spot array elements are separately formed, it does not matter whether the reaction spot array elements are consecutively formed on the same carrier. For "arraying the reaction spot array elements so as to have translation symmetry", the reaction spot array elements need to be arrayed so as to be movable by a movement parallel to each other. By arraying the reaction spot array elements so as to have translation symmetry in a 1-axis direction, 2-axis directions, or 3-axis directions, a larger number of reaction spots can be arrayed with the entire device remaining compact.

The fourth invention is a lightguide aggregate inspection device, in which, on a light-receiving surface of the light-receiving element array, the respective light-receiving regions provided to correspond to the reaction spot array elements are set in a grid at a prescribed interval according to an array of the reaction spot array elements.

Herein, the region forming a "grid" itself is a boundary region having a prescribed width, and the light-receiving regions are preferably separated by the boundary region. This can prevent mutual interference between light-receiving regions.

The fifth invention is a lightguide aggregate inspection device, in which the reaction spot array or the reaction spot array element includes 1 or 2 or more inspection carriers in which predefined types of inspection substances related to the inspection are fixed in multiple different reaction spots at predefined positions identifiable from the outside. Herein, in a case in which the inspection carrier includes multiple particulate carriers, reaction spots are preferably set on a particle basis.

The sixth invention is a lightguide aggregate inspection device, in which the reaction spot array element is provided with 1 reaction spot, the reaction spot is provided with 1 liquid accommodation unit that can accommodate predefined types of solution related to the inspection, and each of the measurement ends is provided to be close to or in contact with a light guidable portion of the liquid accommodation unit.

Herein, "the light guidable portion of the liquid accommodation unit" refers to a portion through which an optical state in the liquid accommodation unit can be guided to the outside thereof, and is, for example, an opening portion of the liquid accommodation unit, the entire wall surface of a liquid accommodation unit made of translucent material, a bottom portion having translucency, or a side surface having translucency, or a partial region of these. The partial region is defined based on the size, shape, or position of the measurement end (including a distance from a liquid accommodation unit of the measurement end, height), a capacity of the liquid accommodation unit, an amount of liquid accommodated in the liquid accommodation unit, and the like. In addition, the "liquid accommodation unit" also includes a "reaction container" that can control temperature.

The seventh invention is a lightguide aggregate inspection device which further includes a processing head provided with 2 or more dispensing elements that are provided to correspond to the respective reaction spot array elements, and can perform suction and discharge of liquid, and in which the dispensing elements are provided to be relatively movable with respect to an accommodation unit group in which multiple accommodation units provided to correspond to the respective reaction spot array elements are arrayed, leading ends of the dispensing elements are provided to be concurrently insertable into the respective liquid accommodation units of the liquid accommodation unit group, and the dispensing elements perform suction and discharge of liquid accommodated in the respective liquid accommodation units, with respect to the reaction spot array elements.

Herein, the "dispensing element" refers to a tool that can perform suction and discharge of liquid, and is, for example, a dispensing tip attached to a dispensing nozzle communicated with a suction and discharge mechanism of gas that is provided in the processing head, or a deformation-type dispensing tip that can concurrently deform using a moving member provided in the processing head.

The processing head is preferably provided to be relatively movable with respect to an accommodation unit group region at least including the accommodation unit group including multiple liquid accommodation units accommodating, for example, sample solution, various types of reagent solution, and various types of cleaning liquid. In addition, in a case in which the dispensing element is a dispensing tip, a tip accommodation unit accommodating a detachably-attached dispensing tip is preferably provided in the accommodation unit group region.

The eighth invention is a lightguide aggregate inspection device, in which the reaction spot array element is an inspection carrier, and is sealed in the dispensing element, the dispensing element performs suction and discharge of liquid with respect to the inspection carrier, the inspection carrier is provided in such a manner that each fixed position is identifiable from the outside of the dispensing element, and the measurement end is provided to be movable while being close to or in contact with the dispensing element, according to an array of reaction spots, by being provided to be relatively movable with respect to the dispensing element by at least the measurement end movement mechanism.

Thus, the dispensing element needs to have translucency. By "sealing in", the inspection carrier contacts liquid sucked by the dispensing element. A sealing unit for holding the inspection carrier so as not to flow out of the dispensing element by the dispensing element discharging liquid is required. In this case, the measurement end movement mechanism is provided not in, for example, the processing head provided with the dispensing element, but in the accommodation unit group region, and after the measurement end is moved close to or in contact with the dispensing element utilizing the movement of the processing head, the measurement end movement mechanism moves the measurement end according to an array of reaction spots, to move close to each reaction spot. The structure of the measurement end movement mechanism can be thereby simplified. In other words, it is sufficient that the measurement end is moved only in an array direction of reaction spots of the reaction spot array elements. As a result, by performing scanning according to an array of reaction spots belonging to 1 reaction spot array element, the measurement ends can be concurrently moved into contact with or close to all of the other reaction spot array elements. The measurement end is preferably positioned in such a manner that the measurement end can move into contact with or close to the dispensing element at an end point of a movement route of the dispensing element within an accommodation unit group region in which the accommodation unit group is provided, and that a leading end of the dispensing element can be inserted, at the position, into an array end liquid accommodation unit which is arrayed at an end of the accommodation unit group. The array end liquid accommodation unit is a reaction container that can control temperature, and can preferably accommodate a substance related to luminescence. As a result, a series of processes from extraction to measurement can be executed smoothly, reasonably, and efficiently.

The ninth invention is a lightguide aggregate inspection device further including a shutter mechanism configured, in a case in which a prescribed reagent moves into contact with or is dispensed to the reaction spot which the measurement end has moved close to or into contact with, or a portion accommodating the reaction spot, to bring the lightguide path connecting the measurement end and the connection end, into a light-guiding state, and in other cases, to bring the lightguide path into a light-shielding state.

Herein, "the reaction spot or the portion accommodating the reaction spot" refers to, for example, a fixed position on an inspection carrier being the reaction spot itself, a liquid accommodation unit, an accommodation unit such as a plate accommodating an inspection carrier provided with the reaction spot, or a dispensing element. The "prescribed reagent" refers to, for example, trigger liquid or a substrate used in the case of chemiluminescence, or a reagent used in luminescence. It is assumed that portions such as an optical system that are related to measurement are accommodated in a dark box or the like, to be shielded from light. In addition, the liquid accommodation unit is preferably shielded from light excluding a light guidable portion such as an opening portion. The lightguide path is preferably shielded from external light as well, excluding the measurement end and the connection end. In a case in which the prescribed reagent is dispensed concurrently into multiple liquid accommodation units, a collective shutter mechanism configured to concurrently bring corresponding multiple lightguide paths into the light-shielding state is preferably included. The shutter mechanism or collective shutter mechanism brings the lightguide path into the light-guiding state in conjunction with a dispensing operation of the dispensing element, and in other cases, brings the lightguide path into the light-shielding state, so that light leakage can be surely prevented.

The tenth invention is a lightguide aggregate inspection method including a reaction step of performing reaction related to inspection in a reaction spot of a reaction spot array including multiple reaction spot array elements having the at least one reaction spot provided at a predefined different position identifiable from an outside, a lightguide step of guiding light that is based on an optical state resulting from reaction in each of the reaction spots, through multiple lightguide paths corresponding to the respective reaction spot array elements and having measurement ends and connection ends that are provided to be movable close to or into contact with, or provided to be close to or in contact with respective reaction spots, to light-receiving regions of a light-receiving surface of a light-receiving element array, each of which has at least one light-receiving element and is provided to be close to or in contact with the connection end, corresponding to each of the reaction spot array elements, a conversion step of converting, at a prescribed period, image region data obtained from the light-receiving elements corresponding to the light-receiving regions of the light-receiving element array, into digital data for each of the light-receiving regions; and a storage step of sequentially storing the converted digital data. Stored digital data is read out by an analysis means in an information processing unit including a CPU and the like, to be calculated and analyzed.

The eleventh invention is a lightguide aggregate inspection method, in which, in a case in which each of the reaction spot array elements includes 2 or more reaction spots, the lightguide step includes a measurement end moving step of concurrently moving the measurement ends close to or into contact with the corresponding reaction spots of the respective reaction spot array elements, by relatively moving a measurement end support body on which a multiple of the measurement ends are supported in an array set according to an array of the reaction spots, with respect to the reaction spot array.

The twelfth invention is a lightguide aggregate inspection method, in which, in a case in which a multiple of the reaction spot array elements in which 2 or more reaction spots are arrayed so as to be congruent to each other are arrayed so as to have translation symmetry to each other, the lightguide step guides light that is based on the optical state, to the light-receiving regions by moving, by the measurement end support body, the measurement ends provided to correspond to the respective spot array elements, in such a manner as to enable the measurement ends to concurrently and sequentially move close to or into contact with the corresponding 2 or more reaction spots provided in the corresponding reaction spot array elements.

Herein, the translation symmetry can be taken in a 1-axis direction, 2-axis directions, or 3-axis directions. By arraying reaction spots in such a manner as to increase the number of axes, the shape of the device can be formed to be compact. In addition, by performing scanning according to an array of reaction spots belonging to 1 reaction spot array element, processing is performed automatically and simultaneously on other corresponding reaction spot array elements.

The thirteenth invention is a lightguide aggregate inspection method, in which the reaction spot array element includes 1 inspection carrier in which predefined types of inspection substances related to the inspection are fixed in multiple different reaction spots at predefined positions identifiable from the outside, and the reaction step performs reaction related to inspection, by dispensing solution to the inspection carrier.

The fourteenth invention is a lightguide aggregate inspection method, in which the reaction spot array elements are sealed in 2 or more dispensing elements which have translucency and can perform suction and discharge of liquid, the dispensing elements are provided to be relatively movable with respect to an accommodation unit group in which liquid accommodation units are arrayed, leading ends of the dispensing elements are provided to be concurrently insertable into the respective accommodation units of the accommodation unit group, and the reaction step performs reaction related to inspection with respect to the reaction spot array elements, by concurrently inserting the dispensing elements into the respective liquid accommodation units to perform suction and discharge of liquid accommodated in the liquid accommodation units.

The fifteenth invention is a lightguide aggregate inspection method, in which 1 reaction spot in the reaction spot array element is provided with 1 liquid accommodation unit that can accommodate predefined types of solution related to the inspection, and the lightguide step guides light that is based on an optical state, and the optical state in each of the reaction spots, from measurement ends provided to be close to or in contact with light guidable portions of the respective liquid accommodation units, to the light-receiving region having at least one light-receiving element provided to correspond to each of the reaction spots, through connection ends of multiple lightguide paths.

The sixteenth invention is a lightguide aggregate inspection method, in which the lightguide step includes a step of bringing a lightguide path connecting the measurement end and the connection end, into a light-guiding state, in a case in which a prescribed reagent contacts the reaction spot which the measurement end has moved close to or into contact with, or a prescribed reagent is dispensed to a portion accommodating the reaction spot, and in other cases, bringing the lightguide path into a light-shielding state.

Advantageous Effects of Invention

According to the first invention or the tenth invention, with respect to a reaction spot array in which multiple reaction spot array elements having at least one reaction spot are arrayed, using a lightguide path provided to correspond to each reaction spot array element, light that is based on an optical state caused at each reaction spot array element is guided to light-receiving regions provided on a light-receiving surface, which are provided to correspond to respective reaction spot array elements, and each of which has at least one light-receiving element having an array area sufficiently smaller than an array area of a reaction spot of the spot array, and aggregated, and image region data obtained through photoelectric conversion are sequentially and concurrently converted at a prescribed period, as digital data, for each reaction spot array element, so as to become analyzable. Thus, for each number of reaction spot array elements further smaller than the number of reaction spots, a temporal change in an optical state of 1 reaction spot, or spatial and temporal changes in optical states of multiple reaction spots is/are received by a light-receiving element array, so that the change(s) can be aggregated temporally and spatially. Thus, not only the expansion in device scale can be suppressed, but also processing with high reliability can be quickly and efficiently performed.

Even in a case in which there are 2 or more reaction spots in each reaction spot array element, and switching is required between reaction spots (switching includes movement and scanning between reaction spots), there is no need to perform switching between reaction spot array elements, the necessity of switching can be lowered to the number of reaction spots in each reaction spot array element, so that a device structure that is based on a switching mechanism can be simplified, and the expansion in device scale can be prevented and processing steps can be saved.

Because processing and measurement can be performed independently and concurrently between reaction spot array elements, reaction spot array elements are physically separated as compared with a case in which reaction spots are treated as the entire reaction spot array, or by shielding light between reaction spot array elements, optical influence between adjacent reaction spot array elements is eliminated, so that processing with higher reliability can be performed, and simultaneous concurrent processing enables efficient and quick processing.

According to the second invention or the eleventh invention, it is only required that a lightguide path and a light-receiving region are provided for each reaction spot array element having 2 or more reaction spots, and by reducing the number of lightguide paths, the number of light-receiving elements, or the number of light-receiving regions, the expansion in device scale can be prevented and device manufacturing costs can be saved. In addition, making measurement ends provided to correspond to respective reaction spot array elements, concurrently movable between reaction spots in the reaction spot array elements eliminates the necessity of providing a separate movement mechanism for each reaction spot array element, so that the expansion in device scale is suppressed. In addition, by changing a spatial change of each reaction spot arrayed in each reaction spot array element, into digital data of each prescribed period, the spatial change can be converted into a temporal change and processing can be simplified and visualized, so that processing with high reliability can be performed.

According to the third invention or the twelfth invention, a reaction spot array includes 2 or more reaction spot array elements arrayed to be congruent to each other, reaction spot array elements are arrayed so as to have translation symmetry to each other, and the measurement end support body is provided in such a manner that measurement ends provided to correspond to the respective reaction spot array elements can sequentially and concurrently move close to or into contact with corresponding reaction spots. Thus, without increasing a device scale or increasing processing steps, using relatively small numbers of lightguide paths and light-receiving regions with respect to a large number of reaction spots, inspection can be efficiently and quickly performed by simple control as if processing is performed on 1 reaction spot array element.

Furthermore, by arraying reaction spot array elements in a dispersed manner so as to have translation symmetry in a 1-axis direction, 2-axis directions, or 3-axis directions according to the increase in the number of reaction spots, the scale as the entire device can be formed into a well-organized compact shape. In addition, by simplifying or standardizing the shape of a measurement end support body and an array of measurement ends to simplify the device structure, and by using a relatively small number of lightguide paths and light-receiving regions having simple shape and arrangement, with respect to a large number of reaction spots, the expansion in device scale and increase in processing steps are suppressed, and control is simplified as if there is 1 reaction spot array element, so that measurement can be performed spatially and temporally-efficiently and quickly.

According to the fourth invention, because light-receiving surfaces of the light-receiving element array is provided to correspond to the reaction spot array elements, and are set in a grid at a prescribed interval according to an array thereof, in addition to the above-described advantages, lightguide paths having measurement ends and connection ends can be easily and surely laid, and an easily-manageable device with high reliability can be manufactured.

According to the fifth invention or the thirteenth invention, because the reaction spot array or the reaction spot array element is an inspection carrier, and can array reaction spots in an aggregated manner, in a case in which a large number of reaction spots are handled, a work space is saved and the expansion in device scale is prevented, so that a compact and efficient device can be formed.

According to the sixth invention or the fifteenth invention, the reaction spot array element is provided with 1 liquid accommodation unit that can accommodate predefined types of solution related to the inspection, and a light guidable portion of each of the liquid accommodation units is provided with a measurement end of the lightguide path. Thus, processing can be performed on an inspection target different for each liquid accommodation unit, while surely preventing cross-contamination. In addition, because a lightguide path can be provided in a fixed manner, for each liquid accommodation unit, a switching mechanism of scanning of measurement ends or the like is not required, and by setting multiple light-receiving regions to a light-receiving surface of the light-receiving element array, processing concurrently performed among multiple liquid accommodation units and inspection with high reliability can be performed with a simple device structure.

According to the seventh invention, by providing a processing head provided with 2 or more dispensing elements that can perform suction and discharge of liquid, and are provided in such a manner that leading ends can be concurrently inserted into respective liquid accommodation units of a planar liquid accommodation body, so as to be relatively movable with respect to the planar liquid accommodation body, processing from reaction to measurement, and furthermore, processing from extraction to measurement can be consistently performed using 1 device, by performing suction and discharge of liquid accommodated in each of the liquid accommodation units by the dispensing element, with respect to the reaction spot array element. Thus, a measurement timing of an optical state can be set from a stage of reaction to an optimum timing, so that quickness and efficiency of processing become higher.

According to the eighth invention or the fourteenth invention, the reaction spot array element is an inspection carrier and is sealed in the dispensing element. Thus, the dispensing element can concurrently perform suction and discharge of liquid with respect to each reaction spot, and because inspection carriers are surely separated, cross-contamination can be surely prevented, so that inspection with high reliability can be performed. In addition, processing from reaction to measurement can be consistently performed by 1 device, and furthermore, by using a dispensing element in which an inspection carrier is not sealed, processing from extraction to measurement can be consistently performed by 1 device.

According to the ninth invention or the sixteenth invention, in a case in which the reaction spot itself which the measurement end has moved close to or into contact with, or an accommodation unit accommodating the reaction spot contacts a prescribed reagent, or the prescribed reagent is dispensed, a lightguide path connecting the measurement end and the connection end is brought into a light-guiding state, and in other cases, brought into a light-shielding state, so that an optical state such as luminescence that is based on the prescribed reagent can be surely received, and destruction or breakage of a highly-sensitive light-receiving element array that can be caused by glaring light in other cases can be prevented.

BRIEF DESCRIPTION OF DRAWINGS

FIG. 1 is a block diagram illustrating a lightguide aggregate inspection device according to a first embodiment of the present invention.

FIG. 2 is a perspective view illustrating a part obtained by further embodying the lightguide aggregate inspection device illustrated in FIG. 1, by detaching the part.

FIG. 3 is a partially-omitted perspective view illustrating a main part of the lightguide aggregate inspection device that is illustrated in FIG. 2, viewed from an opposite direction.

FIG. 4 is a partially-enlarged perspective view of FIG. 2.

FIG. 5 is a partially-enlarged perspective view of FIG. 4.

FIGS. 6(*a*) to 6(*c*) show an explanatory diagram illustrating an operation of the lightguide aggregate inspection device according to the first embodiment of the present invention.

FIG. 7 is a block diagram illustrating a lightguide aggregate inspection device according to a second embodiment of the present invention.

FIGS. 8(*a*) to 8(*c*) show a partially-omitted perspective view illustrating a part obtained by further embodying the lightguide aggregate inspection device illustrated in FIG. 7, by detaching the part.

FIG. 9 is a perspective view illustrating the lightguide aggregate inspection device illustrated in FIGS. 8(*a*) to 8(*c*), viewed from an opposite direction, and is a diagram illustrating a light-receiving element array.

FIG. 10 is a side view illustrating a part of an accommodation unit group region of the lightguide aggregate inspection device illustrated in FIGS. 8(*a*) to 8(*c*).

DESCRIPTION OF EMBODIMENTS

Subsequently, a lightguide aggregate inspection device 10 according to a first embodiment of the present invention will be described based on FIGS. 1 to 6(*c*).

FIG. 1 is a block diagram illustrating the lightguide aggregate inspection device 10.

The lightguide aggregate inspection device 10 broadly, for example, includes an accommodation unit group region 3, an array processing device 5, multiple (n) reaction spot array elements $\mathbf{2}_1$ to $\mathbf{2}_n$, a digital data conversion unit 75, a CPU+program+memory 9, and an operation panel 14. The accommodation unit group region 3 includes accommodation unit groups $\mathbf{3}_1$ to $\mathbf{3}_n$ ("n" corresponds to the number of reaction spot array elements to be described later) which are multiple accommodation units accommodating various types of solution and various types of dispensing tips and arrayed in n columns on a stage in a Y-axis direction. The array processing device 5 includes a processing head 52 and a processing head movement mechanism 53. The processing head 52 is provided to be movable in a horizontal direction, for example, in the Y-axis direction with respect to the accommodation unit group region 3. In the processing head 52, dispensing tips $\mathbf{4}_1$ to $\mathbf{4}_n$ having translucency and corresponding to multiple (n in this example) dispensing elements are provided in such a manner that their leading ends are insertable into the respective accommodation units. The processing head movement mechanism 53 makes the processing head 52 itself movable in an X-axis direction. The multiple (n) reaction spot array elements $2_1$ to $2_n$ are sealed in narrow tubes of the dispensing tips $4_1$ to $4_n$, and form a reaction spot array 2 in which reaction related to inspection is performed, and multiple reaction spots provided at predefined different positions identifiable from the outside are arrayed. The digital data conversion unit 75 converts image region data obtained from the light-receiving elements corresponding to light-receiving regions to be described later, at a prescribed period, to obtain digital data for each of the light-receiving regions. The CPU+program+memory 9 serve as a so-called information processing unit that performs information processing for various types of control. The operation panel 14 performs an operation such as a user instruction to the CPU+program+memory 9.

The accommodation unit group region 3 includes a light-receiving element array 7, lightguide paths $6_1$ to $6_n$, a measurement end support body 63, and a measurement end Z-axis movement mechanism 65. The light-receiving element array 7 includes a light-receiving surface 72 on which multiple light-receiving regions $72_1$ to $72_n$ are provided to correspond to the reaction spot array elements $2_1$ to $2_n$. The multiple light-receiving regions $72_1$ to $72_n$ each include at least one light-receiving element, and receive light obtained based on an optical state that can result from reaction in each of the reaction spots. The lightguide paths $6_1$ to $6_n$ respectively include n measurement ends $62_1$ to $62_n$ and connection ends $64_1$ to $64_n$. The n measurement ends $62_1$ to $62_n$ are respectively provided to be movable into contact with or close to the narrow tubes of the n dispensing tips $4_1$ to $4_n$, and accordingly to be movable close to the sealed-in reaction spot array elements $2_1$ to $2_n$. The connection ends $64_1$ to $64_n$ are provided to be close to the corresponding light-receiving regions $72_1$ to $72_n$ of the light-receiving surface 72. The measurement end support body 63 supports the multiple measurement ends $62_1$ to $62_n$ in such a manner that the multiple measurement ends $62_1$ to $62_n$ are arrayed at an interval set according to an array of the reaction spot array elements $2_1$ to $2_n$. The measurement end Z-axis movement mechanism 65 causes the measurement end support body 63 to make the measurement ends $62_1$ to $62_n$ movable in a Z-axis direction in such a manner as to concurrently and sequentially move close to respective reaction spots 22 of the sealed-in reaction spot array elements $2_1$ to $2_n$ of the dispensing tips $4_1$ to $4_n$ that have moved close by the movement in the Y-axis direction of the processing head 52. In addition, the measurement ends $62_1$ to $62_n$ are preferably arrayed at ends of the accommodation unit groups $3_1$ to $3_n$ that correspond to end points of movement routes of the dispensing elements. Furthermore, the measurement ends $62_1$ to $62_n$ are preferably provided at positions corresponding to array end liquid accommodation units 3*c* into which leading ends of the dispensing tips $4_1$ to $4_n$ can be inserted at the positions, and at positions where the measurement ends $62_1$ to $62_n$ can move into contact with the dispensing tips $4_1$ to $4_n$ in a case in which the dispensing tips $4_1$ to $4_n$ are at the positions.

Each of the reaction spot array elements $2_1$ to $2_n$ is an inspection carrier. For example, the reaction spot array elements $2_1$ to $2_n$ are obtained by arraying multiple particles (the same number of particles in each reaction spot array element) having the same shape in a line in the Z-axis direction within the narrow tubes as described later. Each particle corresponds to a reaction spot at which a prescribed inspection substance is fixed. Thus, 2 or more of the reaction spots are arrayed so as to be congruent to each other. In addition, respective reaction spots of these reaction spot array elements $2_1$ to $2_n$ are arrayed so as to have translation symmetry to each other in the X-axis direction and the Z-axis direction. The diameter of the particle is, for example, 0.5 mm to 10 mm, and is preferably, for example, 1 mm.

The processing head 52 of the lightguide aggregate inspection device 10 includes a suction and discharge mechanism 43 that performs suction and discharge of liquid with respect to the dispensing tips $4_1$ to $4_n$ serving as the dispensing elements. The dispensing tips $4_1$ to $4_n$ are arrayed and supported on a dispensing tip support member in the X-axis direction at an interval set according to an array of the accommodation unit groups $3_1$ to $3_n$. For example, nozzles communicated with the suction and discharge mechanism 43 are arrayed on the dispensing tip support member, and the dispensing tips are supported with being attached to lower end portions of the nozzles.

In addition, the processing head 52 includes a dispensing element Z-axis movement mechanism 42, a temperature raising and lowering body 8, a vertically movable body forward and backward drive mechanism 82, a temperature controller 83, and a magnetic force mechanism 44. The dispensing element Z-axis movement mechanism 42 concurrently moves the dispensing tips $4_1$ to $4_n$ in the Z-axis direction. The temperature raising and lowering body 8 is provided for performing temperature control of the narrow tubes of the respective dispensing tips $4_1$ to $4_n$ in which the reaction spot array elements $2_1$ to $2_n$ are sealed. The vertically movable body forward and backward drive mechanism 82 is provided for moving the temperature raising and lowering body 8 forward or backward for moving the temperature raising and lowering body 8 close to or into contact with each of the dispensing tips $4_1$ to $4_n$. The temperature controller 83 is provided for controlling temperature rising and lowering of the temperature raising and lowering body 8. The magnetic force mechanism 44 is provided for applying magnetic force into the dispensing tips $4_1$ to $4_n$.

The CPU+program+memory 9 include an extraction/reaction control unit 91, a measurement control unit 92, a storage means 93, and an analysis means 94. The extraction/reaction control unit 91 issues an instruction of extraction or reaction to the temperature controller 83, the vertically movable body forward and backward drive mechanism 82, the suction and discharge mechanism 43, the dispensing element Z-axis movement mechanism 42, the magnetic force mechanism 44, and the processing head movement mechanism 53. The measurement control unit 92 issues an instruction of measurement to the measurement end Z-axis movement mechanism 65, the dispensing element Z-axis movement mechanism 42, the light-receiving element array 7, and the analysis means 94. The storage means 93 sequentially stores digital data obtained by converting image region data from the respective light-receiving regions $72_1$ to $72_n$ of the light-receiving element array 7 at a prescribed period set by a pulse signal that is based on the measurement control unit 92, in association with the reaction spot array elements $2_1$ to $2_n$. The analysis means 94 analyzes the inspection through calculation based on the digital data stored in the storage means 93.

Subsequently, a lightguide aggregate inspection device 11 obtained by further embodying the lightguide aggregate inspection device 10 according to the first embodiment of the present invention that is illustrated in FIG. 1 will be described based on FIGS. 2 to 5.

As illustrated in FIG. 2, the lightguide aggregate inspection device 11 is incorporated in a casing 12 having a function of a dark box that can block the invasion of light from the outside, and includes a touch-type tablet 141 corresponding to the operation panel 14.

As illustrated in FIGS. 2 and 3, an accommodation unit group region 31 is provided on the lower side within the casing 12, and on a horizontal plate-like stage 13 attached at an interval set according to a depth of a container, from a bottom 12*a* of the casing 12. In the accommodation unit group region 31, the accommodation unit groups $\mathbf{31}_1$ to $\mathbf{31}_{16}$ (in the case of n=16 in FIG. 1) having cartridge-like containers extending in the Y-axis direction are arrayed in the X-axis direction in multiple columns (16 columns in this example). Each of the accommodation unit groups $\mathbf{31}_1$ to $\mathbf{31}_{16}$ includes a cartridge-like container including a tip accommodation unit group 31*a*, a liquid accommodation unit group 31*b*, and a reaction container 31*c*. In the tip accommodation unit groups 31*a*, attachment opening portions provided in wide tubes of the dispensing tips $\mathbf{41}_1$ to $\mathbf{41}_{16}$ each including a narrow tube and a wide tube are accommodated or can be accommodated so as to be on the upper side. In the liquid accommodation unit groups 31*b*, specimen solution and various types of reagent solution are accommodated. The reaction containers 31*c* serve as the array end liquid accommodation units that are provided at end portions of the containers, accommodate reagent solution necessary for measurement, and can perform temperature control. The things accommodated in each of these accommodation units are accommodated in a processing order in the Y-axis direction corresponding to a movement route of the dispensing tips $\mathbf{41}_1$ to $\mathbf{41}_{16}$.

Furthermore, as the array processing device 51, there is included a processing head 521 provided to be movable in the Y-axis direction with respect to the accommodation unit group region 31, and on which multiple (16 in this example) dispensing tips $\mathbf{41}_1$ to $\mathbf{41}_{16}$ having translucency are provided. The processing head 521 moves along a movement route extending in the Y-axis direction, in such a manner that the dispensing tips $\mathbf{41}_1$ to $\mathbf{41}_{16}$ can be sequentially inserted into the respective accommodation unit groups $\mathbf{31}_1$ to $\mathbf{31}_{16}$, and proceeds to the reaction container 31*c*, where measurement is performed.

The array processing device 51 includes a processing head movement mechanism 53 in which, for example, a ball screw and a timing belt are attached to the casing 12 in the Y-axis direction, for driving the processing head 521 in the Y-axis direction. The processing head 521 includes a nut portion screwed with the ball screw, a Y-axis movement board 52*a* connected with the timing belt, and supporting the entire processing head 521 in such a manner as to suspend therefrom, and a vertical support plate 52*b* attached to the Y-axis movement board 52*a*. The Y-axis movement board 52*a* is provided with a dispensing element Z-axis movement mechanism 421 for moving each of the dispensing tips $\mathbf{41}_1$ to $\mathbf{41}_{16}$ in the Z-axis direction.

The dispensing element Z-axis movement mechanism 421 includes a motor 42*a*, pulleys 42*b* and 42*d*, and a timing belt 42*c*. The motor 42*a* is attached to the Y-axis movement board 52*a*. The pulley 42*b* is connected with a rotational shaft of the motor 42*a*, and penetrates through the Y-axis movement board 52*a* to be positioned on the upper side of the Y-axis movement board 52*a*. The pulley 42*d* is connected with a ball screw 42*e* provided on the lower side of the Y-axis movement board 52*a* to extend in a lower direction, and penetrates through the Y-axis movement board 52*a* to be positioned on the upper side thereof. The timing belt 42*c* is stretched over between these pulleys 42*b* and 42*d*.

The processing head 521 is further provided with a suction and discharge mechanism 431 for performing suction and discharge of liquid with respect to the dispensing tips $\mathbf{41}_1$ to $\mathbf{41}_{16}$ serving as the dispensing elements. The suction and discharge mechanism 431 includes a Z-axis movement board 43*a*, a motor 43*b*, a piston rod drive plate 43*g*, 16 piston rods 43*c*, a cylinder support member 43*i*, and a tip detaching and attaching plate 43*e*. The Z-axis movement board 43*a* is connected with a nut portion screwed with the ball screw 42*e* of the dispensing element Z-axis movement mechanism 421 to be provided to be movable in the Z-axis direction. The motor 43*b* is attached to the lower side of the Z-axis movement board 43*a*. The piston rod drive plate 43*g* is connected with a nut portion screwed with a ball screw 43*h* rotationally-driven by the motor 43*b*, to vertically move. The 16 piston rods 43*c* are caused to concurrently slide in the Z-axis direction within 16 cylinders 43*d* by the drive plate 43*g*. The cylinder support member 43*i* is supported by the Z-axis movement board 43*a*, and the cylinders 43*d* are attached to the cylinder support member 43*i*. The cylinder support member 43*i* supports 16 nozzles provided at lower ends of the cylinders 43*d*. In the tip detaching and attaching plate 43*e*, through-holes are formed. The through-holes have the size that enables the nozzles protruding toward the lower side of the cylinders 43*d*, to penetrate, but have the size that prevents the dispensing tips $\mathbf{41}_1$ to $\mathbf{41}_{16}$ attached to the nozzles, from penetrating. The tip detaching and attaching plate 43*e* is supported by the piston rod drive plate 43*g*, and provided to be movable in a lower direction by pressing a detaching and attaching rod 43*j* by lowering the piston rod drive plate by a prescribed distance or more. The lower end of the detaching and attaching rod 43*j* is attached to the tip detaching and attaching plate 43*e*. On the upper side thereof, the detaching and attaching rod 43*j* is supported with being elastically-biased upward by the cylinder support member 43*i*. The upper end thereof is at a position separated from the piston rod drive plate 43*g* by the prescribed distance. Herein, a reference sign 43*f* denotes a flow tube to which a pressure sensor for detecting the pressure within the dispensing tips $\mathbf{41}_1$ to $\mathbf{41}_{16}$ is attached.

Attachment opening portions of the 16 dispensing tips $\mathbf{41}_1$ to $\mathbf{41}_{16}$ fit with the 16 nozzles protruding downward at the lower ends of the cylinders 43*d*, so that the 16 dispensing tips $\mathbf{41}_1$ to $\mathbf{41}_{16}$ are attached. Thus, together with the Z-axis movement board 43*a*, the dispensing tips $\mathbf{41}_1$ to $\mathbf{41}_{16}$ can vertically move in the Z-axis direction with respect to the processing head 521, and leading ends thereof can be inserted into liquid accommodation units provided in the accommodation unit group region 31. Suction and discharge of liquid can be performed by the suction and discharge mechanism 431. As a result, the dispensing tips $\mathbf{41}_1$ to $\mathbf{41}_{16}$ can move into contact with particles serving as multiple (50 in this example) reaction spots 22 constituting each of the reaction spot array elements $\mathbf{21}_1$ to $\mathbf{21}_{16}$ sealed in the dispensing tips $\mathbf{41}_1$ to $\mathbf{41}_{16}$ (refer to FIG. 5).

As illustrated in FIG. 5, the dispensing tips $\mathbf{41}_1$ to $\mathbf{41}_{16}$ each include a narrow tube 41*a* and a wide tube 41*b* connected with the narrow tube 41*a* and provided with the attachment opening portion detachably attached to the nozzle. In the narrow tube 41*a* of each of the dispensing tips $\mathbf{41}_1$ to $\mathbf{41}_{16}$, reaction related to inspection is performed, and multiple (16 in this example) reaction spot array elements $\mathbf{21}_1$ to $\mathbf{21}_{16}$ are sealed and arrayed while having translation symmetry to each other in the X-axis direction. The multiple reaction spot array elements 21$_1$ to 21$_{16}$ form the reaction spot array 20 in which particles serving as multiple (e.g., 50 in this example) reaction spots 22 provided at predefined different positions identifiable from the outside are arrayed in a line in the Z-axis direction so as to be congruent. In a similar manner, the reaction spots are arrayed while having translation symmetry also in the Z-axis direction. In other words, in the lightguide aggregate inspection device 11 according to the present embodiment, the reaction spots are arrayed while having translation symmetry in 2 axis directions, i.e., in the X-axis direction and the Z-axis direction. The reaction spot array elements 21$_1$ to 21$_{16}$ are arrayed while having translation symmetry in the X-axis direction.

Referring back to FIG. 3, the accommodation unit group region 31 further includes a light-receiving element array 71 on the bottom 12*a* of the casing 12 that is on the bottom side of the stage 13. In the light-receiving element array 71, multiple (e.g., 16 in this example) light-receiving elements are arrayed in such a manner as to forma common light-receiving surface. The light-receiving element array 71 includes at least one light-receiving element so as to correspond to the reaction spot array elements 21$_1$ to 21$_{16}$, and a light-receiving surface 72 is provided in a dark box 71*a*. The light-receiving surface 72 is provided with the multiple (16 in this example) light-receiving regions 72$_1$ to 72$_{16}$ that receive light obtained based on an optical state that can result from reaction in each of the reaction spots.

The description will be given of a case in which a CCD image sensor is used as the light-receiving element array 71. For example, a CCD image sensor having a light-receiving surface of 6.4 mm×4.8 mm, and in which 772×580 light-receiving elements are arrayed is used. In this case, on the light-receiving surface, for example, as illustrated in FIG. 6(*a*), 16 light-receiving regions 72$_1$ to 72$_{16}$ are set in a grid (matrix) of 4 rows×4 columns. Each light-receiving region corresponds to light-receiving elements of portions excluding a boundary, among 193×145 light-receiving elements. As the digital data conversion unit 75, a shift register that sequentially transfers charge by gate control, an amplifier that performs voltage amplification, and an AD converter that converts a charge amount into digital data are included. The prescribed period can be defined based on, for example, a time interval specified by an instruction from the operation panel 140 or an instruction issued by a measurement control unit of the CPU+program+memory 9. The prescribed period is defined based on the type of luminescence, a reagent, the mode of luminescence, a time required for exposure, transfer, or reading out, a reaction time in the reaction spot, an optical state, a life thereof, and the like. Furthermore, the prescribed period is defined according to a light measurement mode considering the speed of scanning between reaction spots that is performed by the measurement end Z-axis movement mechanism 65, a distance between reaction spots, or the movement mode thereof. In other words, digital data conversion is preferably performed at a period synchronized with the movement of the measurement end with respect to 1 reaction spot that is performed by the measurement end Z-axis movement mechanism 65. For example, measurement is performed in such a manner that scanning is performed in the Z-axis direction using an optical fiber with a diameter of 1 mm that is provided at the measurement end, with respect to 50 particles with a diameter of 1 mm. In this case, the measurement end is relatively moved with a distance from a light-receiving position to the next light-receiving position being set to 0.1 mm, and intermittently moved while stopping for a time of 10 msec as a light-receiving time (stop time required for photon counting) considering a plateau state of chemiluminescence, for example. In this manner, 10 measurements are performed for 1 particle. These values are set considering indeterminacy that is based on the fact that the position of the particle is not necessarily fixed, the size of the optical fiber, and the like. As a result, luminance of Gauss function type luminescence is obtained for 1 particle, and based on the luminance, accurate measurement of luminescence or the like can be performed. For this purpose, the measurement control unit 96 issues a pulse signal of such a timing, to the dispensing element Z-axis movement mechanism 42 and the storage means 97, thereby performing measurement. As a result, as all 50 particles, 500 times of light receiving or digital data conversion are performed in about 30 seconds to about 50 seconds (considering the plateau state of chemiluminescence) including a movement time.

As illustrated in FIGS. 3 to 5, the accommodation unit group region 31 further includes multiple (16 in this example) lightguide paths 61$_1$ to 61$_{16}$ having respective measurement ends 62$_1$ to 62$_{16}$ provided to be movable into contact with narrow tubes of the respective dispensing tips 41$_1$ to 41$_{16}$, and respective connection ends provided to be close to the light-receiving regions 72$_1$ to 72$_{16}$ of the light-receiving surface 72. The connection ends are accommodated in the dark box 71*a*. The measurement ends 62$_1$ to 62$_{16}$ are arrayed and supported on a measurement end support body 631 in the X-axis direction at an interval set according to an array of the reaction spot array elements 21$_1$ to 21$_{16}$. In addition, in FIGS. 3 to 5, a middle portion of the lightguide path 61$_1$ to 61$_{16}$ is partially omitted for the sake of drawing, and for facilitating visualization of the device for descriptive purposes.

In addition, the accommodation unit group region 31 is provided with a measurement end Z-axis movement mechanism 651 that can scan reaction spots by making the measurement end support body 631, i.e., the multiple (16 in this example) measurement ends 62$_1$ to 62$_{16}$ movable in the Z-axis direction being the axis direction of the dispensing tips 41$_1$ to 41$_{16}$. The measurement ends 62$_1$ to 62$_{16}$ are provided to be on the upper portion of an accommodation unit 30*c* provided on the rear end side in the Y-axis direction of the accommodation unit groups 31$_1$ to 31$_{16}$, in other words, the accommodation unit 30*c* in which reagent solution sucked for performing measurement processing is accommodated.

The measurement end Z-axis movement mechanism 651 includes an arm member 65*a*, an arm holder 65*b*, a motor 65*c*, abase portion 65*d*, a ball screw 65*h*, guide pillars 65*e* and 65*f*, and an attachment tool 65*g*. The arm member 65*a* is connected with the measurement end support body 631. The arm holder 65*b* slidably holds the arm member 65*a*, and is provided with an elastic member constantly and elastically biasing in the Y-axis direction so as to move forward toward the dispensing tips 41$_1$ to 41$_{16}$. The motor 65*c* rotationally drives a nut portion screwed with the ball screw 65*h*, for vertically moving the ball screw 65*h* and the arm holder 65*b* in the Z-axis direction. The motor 65*c* is attached to the base portion 65*d*. The base portion 65*d* is provided with a hole through which the ball screw 65*h* penetrates, and is fixed on the stage. The ball screw 65*h* is screwed with the nut portion rotationally driven by the motor 65*c*, and is vertically driven so that its leading end is pivotally supported on the lower side of the arm holder 65*b*. The lower ends of the guide pillars 65*e* and 65*f* are provided on the base portion. The guide pillars 65*e* and 65*f* penetrate through the arm holder 65*b*. The upper ends of the guide pillars 65*e* and 65*f* are attached to the attachment tool 65*g*. The attachment tool 65*g* is attached to the casing 12.

As a result, if the dispensing tips $\mathbf{41}_1$ to $\mathbf{41}_{16}$ are moved while the processing head 521 performing the processing in the Y-axis direction, and finally, the dispensing tips $\mathbf{41}_1$ to $\mathbf{41}_{16}$ reach the reaction container 31*c* serving as the liquid accommodation unit, the respective narrow tubes 41*a* of the dispensing tips $\mathbf{41}_1$ to $\mathbf{41}_{16}$ press the measurement ends $\mathbf{62}_1$ to $\mathbf{62}_{16}$, whereby the measurement ends $\mathbf{62}_1$ to $\mathbf{62}_{16}$ receive elastic repulsion, and move into contact.

Thus, if the measurement end support body 631 moves in the Z-axis direction, the measurement ends $\mathbf{62}_1$ to $\mathbf{62}_{16}$ arrayed according to the array of the reaction spot array elements $\mathbf{21}_1$ to $\mathbf{21}_{16}$ move in the Z-axis direction with respect to the respective array elements $\mathbf{21}_1$ to $\mathbf{21}_{16}$, thereby performing scanning while concurrently and sequentially moving close to and away from particles corresponding to the reaction spots 22 belonging to the respective reaction spot array elements $\mathbf{21}_1$ to $\mathbf{21}_{16}$. In addition, the guide pillars 65*e* and 65*f* are formed to have lengths longer than the length in the Z-axis direction of the reaction spot array elements $\mathbf{21}_1$ to $\mathbf{21}_{16}$.

The processing head 521 is further provided with a temperature raising and lowering body 81 having a heating sheet stretched all over the surface. A vertically movable body forward and backward drive mechanism 821 is included. The vertically movable body forward and backward drive mechanism 821 enables the temperature raising and lowering body 81 to be operated forward and backward so as to concurrently move close to or to be movable into contact with the dispensing tips $\mathbf{41}_1$ to $\mathbf{41}_{16}$. The vertically movable body forward and backward drive mechanism 821 includes a motor 82*a* for moving each of the temperature raising and lowering body 81 so as be operated forward and backward. The temperature raising and lowering body 81 does not move in the Z-axis direction, and is provided to be positioned in a region corresponding to a movement range of the measurement ends $\mathbf{62}_1$ to $\mathbf{62}_{16}$.

Furthermore, the processing head 521 is provided with a magnetic force mechanism 441 for applying magnetic force into the dispensing tips $\mathbf{41}_1$ to $\mathbf{41}_{16}$ attached to the nozzles. The magnetic force mechanism 441 includes 16 permanent magnets 44*a*, a magnet array member 44*b*, a ball screw 44*d*, an actuator 44*c*, and 2 connecting bars 44*f*. The 16 permanent magnets 44*a* are arrayed at an interval set according to the array of the dispensing tips $\mathbf{41}_1$ to $\mathbf{41}_{16}$. The magnet array member 44*b* supports the 16 permanent magnets 44*a*. The ball screw 44*d* is provided in the Y-axis direction for operating the magnet array member 44*b* forward and backward in the X-axis direction with respect to the dispensing tips $\mathbf{41}_1$ to $\mathbf{41}_{16}$. One end of the ball screw 44*d* is pivotally supported by the magnet array member 44*b*, and the other end is pivotally supported by a ball screw shaft support plate 44*e*. In the actuator 44*c*, a motor for rotationally driving a nut portion screwed with the ball screw 44*d* is built in. The actuator 44*c* is supported by the Y-axis movement board 52*a*, and horizontally moves the ball screw 44*d* in the Y-axis direction. The 2 connecting bars 44*f* penetrate through the actuator 44*c* to connect the ball screw shaft support plate 44*e* and the magnet array member 44*b*.

Subsequently, the description will be given of an operation performed in the case of performing the inspection of specific SNPs related to an effect of a prescribed medicine, for genomes of 16 subjects, thereby inspecting the validity as to whether to use the medicine, using the lightguide aggregate inspection device 11 according to the first embodiment.

In the tip accommodation unit group 31*a*, an extraction dispensing tip, a PCR dispensing tip, a boring tip, and the dispensing tips $\mathbf{41}_1$ to $\mathbf{41}_{16}$ in which the reaction spot array elements $\mathbf{21}_1$ to $\mathbf{21}_{16}$ are sealed are accommodated in advance with the attachment opening portion facing upward. In each liquid accommodation unit of the liquid accommodation unit group 31*b*, a specimen such as an oral mucous membrane collected from a subject, a genome extraction reagent, magnetic particle suspension liquid, primer containing liquid serving as a PCR reagent, and mineral oil and cleaning liquid such as restriction enzyme solution are sequentially accommodated in advance, and part of the accommodation units are empty. In addition, a reaction container such as a PCR container in which temperature control can be performed is included. In the dispensing tips $\mathbf{41}_1$ to $\mathbf{41}_{16}$, probes having base sequences of 2 types of SNP polytypic of multiple locations related to the medicine are fixed at each particle while sandwiching an appropriate spacer particle. Each particle has, for example, a spherical shape, and a diameter is, for example, 1 mm.

In step S1, the processing head movement mechanism 53 moves the processing head 521 in the Y-axis direction so as to be positioned on an upper portion of a first tip accommodation unit of the tip accommodation unit group 31*a* in which an unused extraction dispensing tip is accommodated. By lowering the 16 nozzles provided in the processing head 521, by the dispensing element Z-axis movement mechanism 421, an extraction dispensing tip is attached. If the 16 nozzles are elevated again, and a lower end of the dispensing tip reaches the upper portion of the tip accommodation unit, the dispensing tip moves in the Y-axis direction.

In step S2, by moving the processing head 521 to the position of 1 liquid accommodation unit belonging to the liquid accommodation unit group 31*b* accommodating the genome extraction reagent, and lowering the processing head 521, the leading end of the dispensing tip is inserted into the liquid accommodation unit, and the corresponding extraction reagents are concurrently sucked using the suction and discharge mechanism 430. The dispensing tip is transferred to 1 liquid accommodation unit of the liquid accommodation unit group 31*b* in which the specimen solution is accommodated, and the lower end of the dispensing tip is inserted into the liquid accommodation unit, and the solution is discharged. Furthermore, in a similar manner, magnetic particle suspension liquid for extracting a DNA of each subject serving as an objective substance that is accommodated in 1 liquid accommodation unit of the liquid accommodation unit group 31*b* is sucked into the dispensing tip, and transferred to the liquid accommodation unit in which the specimen solution is accommodated, to be discharged. Furthermore, suction and discharge are repeated to perform agitation, so that the DNA of each subject serving as an objective substance is bonded to a magnetic particle. In addition, as necessary, suction and discharge are further repeated using cleaning liquid for removing foreign substances.

In step S3, using the actuator 44*c* of the magnetic force mechanism 441, the magnet array member 44*b* is moved close to the extraction dispensing tip, and the magnet 44*a* is moved close to the narrow tube of the dispensing tip, so that a magnetic field is generated within the narrow tube, and the magnetic particle to which the DNA of each subject is bonded is stuck to the inside wall of the narrow tube to be separated. While remaining stuck to the inside wall, the separated magnetic particle is transferred by the processing head 521 to a next 1 liquid accommodation unit in which separation liquid of the liquid accommodation unit group 31*b* is accommodated, and in a state in which the magnet array member 44*b* is separated from the extraction dispensing tip by the magnetic force mechanism 441, suction and discharge of separation solution, and furthermore, of cleaning liquid as necessary, are repeated. The DNA of each subject being an objective substance is thereby suspended in separation solution, and the magnetic force mechanism 441 moves the processing head 52 again with the magnetic particle being stuck to the inside wall. In the tip accommodation unit group 31*a*, by lowering the tip detaching and attaching plate 43*e*, the extraction dispensing tip is detached from the nozzle to be discarded.

In step S4, by lowering an unused PCR dispensing tip accommodated in 1 tip accommodation unit of the tip accommodation unit group 31*a*, by the dispensing element Z-axis movement mechanism 421 of the processing head 521, the nozzle is fit with and attached to an attachment opening portion of the dispensing tip, the processing head 521 is elevated and moved in the Y-axis direction, the DNA solution accommodated in the liquid accommodation unit of the liquid accommodation unit group 31*b* is sucked by the suction and discharge mechanism 431, and the dispensing tip is elevated by the dispensing element Z-axis movement mechanism 421, and moved to the PCR liquid accommodation unit provided in the liquid accommodation unit group 31*b*, so that the DNA solution is discharged. In a similar manner, reagent solution such as primer having a corresponding base sequence for amplifying a base sequence containing each SNP is discharged to the PCR reaction container, and a DNA fragment having a base sequence containing each corresponding SNP is amplified and generated through prescribed temperature control cycle that is based on the PCR method.

In step S5, DNA fragment solution containing various types of generated SNP is dispensed into by the PCR dispensing tip and agitated in 1 liquid accommodation unit provided in the liquid accommodation unit group 31*b* accommodating chemiluminescent substance solution connected with an adaptor having a complementary base sequence with a base sequence specific to each DNA fragment, and the various types of SNP are labeled using a chemiluminescent substance. Herein, as the chemiluminescent substance, an enzyme and horseradish peroxidase are used, and as a substrate, luminol/hydrogen peroxide is used, and detection is performed by the CLEIA method.

In step S6, the processing head 521 is returned again to the tip accommodation unit group 31*a*, and the attached PCR dispensing tip is detached by the tip detaching and attaching plate 43*e* to be discarded into an empty tip accommodation unit.

In step S7, the processing head 521 is elevated, and then, moved again in the Y-axis direction to be positioned on the upper portion of the tip accommodation unit, which is 1 tip accommodation unit in the tip accommodation unit group 31*a*, and in which the dispensing tips $\mathbf{41}_1$ to $\mathbf{41}_{16}$ in which the reaction spot array elements $\mathbf{21}_1$ to $\mathbf{21}_{16}$ are sealed are accommodated. By lowering the nozzles by the dispensing element Z-axis movement mechanism 421, the nozzles fit with the attachment opening portion thereof and the dispensing tips $\mathbf{41}_1$ to $\mathbf{41}_{16}$ are attached to the nozzles.

In step S8, the dispensing tips $\mathbf{41}_1$ to $\mathbf{41}_{16}$ are moved in the Y-axis direction, and moved to the upper portion of the liquid accommodation unit of the liquid accommodation unit group 31*b* of the accommodation unit groups $\mathbf{31}_1$ to $\mathbf{31}_{16}$ in which the labeled various types of SNP fragment are accommodated, leading ends of the dispensing tips $\mathbf{41}_1$ to $\mathbf{41}_{16}$ are inserted into the liquid accommodation unit using the dispensing element Z-axis movement mechanism 421, and suction and discharge are repeated by the suction and discharge mechanism 430, whereby the reaction spot array elements $\mathbf{21}_1$ to $\mathbf{21}_{16}$ having the particulate carrier are caused to experience contact reaction with the solution. At this time, according to an instruction from the extraction/reaction control unit 91, the motor 82*a* serving as the vertically movable body forward and backward drive mechanism 82 moves the temperature raising and lowering body 81 forward to and into close contact with the dispensing tips $\mathbf{41}_1$ to $\mathbf{41}_{16}$, thereby maintaining the temperature in the dispensing tips $\mathbf{41}_1$ to $\mathbf{41}_{16}$ at a prescribed temperature.

In step S9, the dispensing tips $\mathbf{41}_1$ to $\mathbf{41}_{16}$ are moved in the Y-axis direction using the processing head movement mechanism 53, and moved to 1 liquid accommodation unit of the liquid accommodation unit group 31*b* in which cleaning liquid is accommodated, and in a state in which the temperature raising and lowering body 81 is separated from the dispensing tips $\mathbf{41}_1$ to $\mathbf{41}_{16}$, suction and discharge are repeated, whereby cleaning is performed. FIG. 3 illustrates the positions of the dispensing tips $\mathbf{41}_1$ to $\mathbf{41}_1$, the measurement ends $\mathbf{62}_1$ to $\mathbf{62}_{16}$, and the temperature raising and lowering body 81 in step S9 at this stage.

In step S10, the dispensing tips $\mathbf{41}_1$ to $\mathbf{41}_{16}$ are moved to the reaction container 31*c* accommodating the substrate of chemiluminescence, and the leading ends are inserted into the reaction container 31*c*. At this time, the narrow tubes of the dispensing tips $\mathbf{41}_1$ to $\mathbf{41}_{16}$ enter the state of being in contact with the measurement ends $\mathbf{62}_1$ to $\mathbf{62}_{16}$. In addition, the motor 82*a* serving as the vertically movable body forward and backward drive mechanism 82 moves the temperature raising and lowering body 81 forward to and into close contact with the dispensing tips $\mathbf{41}_1$ to $\mathbf{41}_1$, thereby maintaining the temperature in the dispensing tips $\mathbf{41}_1$ to $\mathbf{41}_1$ at a prescribed temperature. The state at this stage corresponds to FIG. 4.

In step S11, the dispensing tips $\mathbf{41}_1$ to $\mathbf{41}_{16}$ suck solution in the reaction container 31*c*. As a result, in the reaction container 31*c*, the sucked liquid reacts with the reaction spot array elements $\mathbf{21}_1$ to $\mathbf{21}_{16}$ sealed in these dispensing tips $\mathbf{41}_1$ to $\mathbf{41}_{16}$.

Then, by moving the measurement end support body 63 in the Z-axis direction by the measurement end Z-axis movement mechanism 65, light is guided to corresponding reaction spots arrayed in the respective reaction spot array elements $\mathbf{21}_1$ to $\mathbf{21}_{16}$ concurrently and sequentially from the measurement ends $\mathbf{62}_1$ to $\mathbf{62}_{16}$ to the connection ends $\mathbf{64}_1$ to $\mathbf{64}_{16}$ through the lightguide paths $\mathbf{61}_1$ to $\mathbf{61}_{16}$ in the light-receiving regions $\mathbf{72}_1$ to $\mathbf{72}_{16}$ provided in the light-receiving surface 72 corresponding to the reaction spot array elements $\mathbf{21}_1$ to $\mathbf{21}_{16}$.

In step S12, in each of the light-receiving regions $\mathbf{72}_1$ to $\mathbf{72}_{16}$, optical states corresponding to 50 particles are sequentially received according to the movement in the Z-axis direction of the measurement ends $\mathbf{62}_1$ to $\mathbf{62}_{16}$ that is performed by the measurement end Z-axis movement mechanism 651. As a result, by performing a relative movement of the measurement ends $\mathbf{62}_1$ to $\mathbf{62}_{16}$, for example, such as a movement of intermittently repeating a movement by a distance of 0.1 mm while taking a stop time (light-receiving time) of 10 msec, at a period that enables 10 times of light receiving for 1 particle with a diameter of 1 mm, according to an instruction from the measurement control unit 92, intensity or luminance of light received for each reaction spot array element is converted by the digital data conversion unit 75 into corresponding digital data, sequentially stored into the storage means 93, and read out by the analysis means 94 to be calculated and analyzed, so that target biological substance to be inspected can be inspected. Herein, the "prescribed period" is defined based on a light measurement mode including, for example, a movement time required for a relative movement of a measurement end that is performed by the measurement end movement mechanism (e.g., 50 msec for adjacent reaction spots, for example), the number of times of light receiving for each reaction spot (e.g., 10 times), the number of reaction spots (e.g., 50), and a stable light receptible time in which chemiluminescence can be stably received (time in which the plateau state of luminescence is maintained, for example, 30 seconds to 50 seconds), and based on this, a stop time for light receiving (digital data conversion) for a reaction spot is defined as, for example, 10 msec, and instructed by the measurement control unit 92.

FIG. 6(*a*) illustrates an array example of particles serving as multiple reaction spots 22 corresponding to the reaction spot array elements $\mathbf{21}_1$ to $\mathbf{21}_{16}$ arrayed in the Z-axis direction in the narrow tubes of the dispensing tips $\mathbf{41}_1$ to $\mathbf{41}_{16}$. Spacers 23 (indicated by a dark color in the drawing) are provided in such a manner as to sandwich the reaction spots 22 (indicated by a pale color in the drawing). The diameter of these particles is, for example, 1 mm. The state in which the measurement end support body 631 sequentially moves particles in the Z-axis direction starting from a first particle 25, and light that is based on an optical state of each particle is guided to a light-receiving surface 721 of the light-receiving element array 71 through optical fibers serving as the lightguide paths $\mathbf{61}_1$ to $\mathbf{61}_{16}$ is schematically illustrated. In addition, a particle 24 at the lowermost end is formed of flexible material and formed to have a relatively large radius provided for sealing the particle in the narrow tube 41*a*. In addition, a particle 25 at the uppermost end is, for example, a particle for marker. In addition, the total length of a portion in which the reaction spots 22 are provided and measurement is performed is, for example, 40 to 50 mm.

FIG. 6(*b*) schematically illustrates the light-receiving regions $\mathbf{72}_1$ to $\mathbf{72}_{16}$ provided in a grid on the light-receiving surface 721 of the light-receiving element array 71 corresponding to the respective reaction spot array elements $\mathbf{21}_1$ to $\mathbf{21}_{16}$. The light-receiving regions $\mathbf{72}_1$ to $\mathbf{72}_{16}$ are provided to be close to the connection ends $\mathbf{64}_1$ to $\mathbf{64}_{16}$ of the respective fibers $\mathbf{61}_1$ to $\mathbf{61}_{16}$. As a result, even if the reaction spot array elements $\mathbf{21}_1$ to $\mathbf{21}_{16}$ are arrayed high-dimensionally and broadly, the light-receiving regions can be provided to correspond to the respective reaction spot array elements in an aggregated manner. Thus, the expansion in device scale can be suppressed.

FIG. 6(*c*) illustrates a schematic diagram of digital data stored in the storage means 97, as a graph. By converting this luminance into a numerical value, and the analysis means 94 performing calculation and analysis, an inspection result can be analyzed and output for each specimen.

FIG. 7 is a block diagram illustrating a lightguide aggregate inspection device 100 according to a second embodiment.

The lightguide aggregate inspection device 100 broadly includes an accommodation unit group region 30, an array processing device 50, a digital data conversion unit 76, a CPU+program+memory 90, and an operation panel 140. The accommodation unit group region 30 corresponds to multiple accommodation units that accommodate or can accommodate various types of solution, various types of dispensing tips, and solution, and includes accommodation unit groups $\mathbf{30}_1$ to $\mathbf{30}_n$ ("n" corresponds to the number of reaction spot array elements to be described later) arrayed in n columns on a stage in the Y-axis direction. The array processing device 50 includes a processing head 54 and a processing head movement mechanism 55. The processing head 54 is provided to be movable in a horizontal direction, for example, in the Y-axis direction with respect to the accommodation unit group region 30. In the processing head 54, dispensing tips $\mathbf{40}_1$ to $\mathbf{40}_n$ corresponding to multiple (n in this example) dispensing elements are provided in such a manner that their leading ends are insertable into the respective accommodation units. The digital data conversion unit 76 converts image region data obtained from the light-receiving elements corresponding to light-receiving regions to be described later, at a prescribed period, to obtain digital data for each of the light-receiving regions. The CPU+program+memory 90 serve as a so-called information processing unit for performing various types of control. The operation panel 140 performs an operation such as a user instruction to the CPU+program+memory 90. In addition, the array processing device 50 and the accommodation unit group region 30 are preferably formed in a dark box.

The accommodation unit group region 30 includes reaction containers $\mathbf{20}_1$ to $\mathbf{20}_n$, a light-receiving element array 70, lightguide paths $\mathbf{60}_1$ to $\mathbf{60}_n$, a collective shutter mechanism 66, a temperature raising and lowering body 80, and a temperature controller 84. The reaction containers $\mathbf{20}_1$ to $\mathbf{20}_n$ are provided at predefined positions of the liquid accommodation unit group (in this example, an end of an array of container groups) as part of the accommodation unit groups $\mathbf{30}_1$ to $\mathbf{30}_n$ provided on the movement routes of the respective dispensing tips $\mathbf{40}_1$ to $\mathbf{40}_n$. In the reaction containers $\mathbf{20}_1$ to $\mathbf{20}_n$, reaction related to inspection is performed, and the reaction containers $\mathbf{20}_1$ to $\mathbf{20}_n$ serve as the array end liquid accommodation unit corresponding to each 1 reaction spot belonging to reaction spot array elements constituting the reaction spot array 20. The light-receiving element array 70 includes a light-receiving surface 74 on which multiple light-receiving regions $\mathbf{74}_1$ to $\mathbf{74}_n$ are provided. The multiple light-receiving regions $\mathbf{74}_1$ to $\mathbf{74}_n$ each include at least one light-receiving element corresponding to each of the reaction containers $\mathbf{20}_1$ to $\mathbf{20}_n$ corresponding to the reaction spot array element, and receive light obtained based on an optical state that can result from reaction in the reaction containers $\mathbf{20}_1$ to $\mathbf{20}_n$, as the reaction spot. The lightguide paths $\mathbf{60}_1$ to $\mathbf{60}_n$ respectively include n measurement ends $\mathbf{67}_1$ to $\mathbf{67}_n$ provided to be close to or in contact with light guidable portions of the n reaction containers $\mathbf{20}_1$ to $\mathbf{20}_n$, and connection ends $\mathbf{68}_1$ to $\mathbf{68}_n$ provided to be close to the corresponding light-receiving regions $\mathbf{74}_1$ to $\mathbf{74}_n$ of the light-receiving surface 74. The collective shutter mechanism 66 brings the lightguide paths $\mathbf{60}_1$ to $\mathbf{60}_n$ into a light-guiding state in a case in which the reaction containers $\mathbf{20}_1$ to $\mathbf{20}_n$ dispense prescribed trigger liquid using the dispensing tips $\mathbf{40}_1$ to $\mathbf{40}_n$, and concurrently brings the lightguide paths $\mathbf{60}_1$ to $\mathbf{60}_n$ into a light-shielding state in a case in which the dispensing of the reaction containers $\mathbf{20}_1$ to $\mathbf{20}_n$ is not performed. The temperature raising and lowering body 80 performs temperature control of solution accommodated in the reaction containers $\mathbf{20}_1$ to $\mathbf{20}_n$. The temperature controller 84 is provided for controlling temperature rising and lowering of the temperature raising and lowering body 80.

The reaction spot array elements are each provided with a corresponding 1 of the reaction containers $\mathbf{20}_1$ to $\mathbf{20}_n$ as 1 reaction spot, and are arrayed in a line in the X-axis direction. Each of the reaction containers $\mathbf{20}_1$ to $\mathbf{20}_n$ corresponds to the reaction spot array element and the reaction spot. In the present embodiment, unlike the first embodiment, no reaction spot is provided in the dispensing tips 40$_1$ to 40$_n$.

The present embodiment is similar to the first embodiment in that the processing head 54 of the lightguide aggregate inspection device 100 includes a suction and discharge mechanism 43 that performs suction and discharge of liquid with respect to the dispensing tips 40$_1$ to 40$_n$ serving as the dispensing elements, a magnetic force mechanism 44, and a dispensing element Z-axis movement mechanism 42. In the second embodiment, a shutter driving member 45 is further included. The shutter driving member 45 drives the collective shutter mechanism 66 to bring the lightguide paths 60$_1$ to 60$_n$ into the light-guiding state in a case in which trigger liquid serving as the prescribed reagent is dispensed to the reaction containers 20$_1$ to 20$_n$, and to bring the lightguide paths 60$_1$ to 60$_n$ into the light-shielding state in other cases.

The CPU+program+memory 90 include an extraction/reaction control unit 95, a measurement control unit 96, a storage means 97, and an analysis means 98. The extraction/reaction control unit 95 issues an instruction of extraction or reaction to the temperature controller 84, the suction and discharge mechanism 43, the dispensing element Z-axis movement mechanism 42, the magnetic force mechanism 44, and the processing head movement mechanism 55. The measurement control unit 96 issues an instruction of measurement to the dispensing element Z-axis movement mechanism 42, the temperature controller 84, the light-receiving element array 70, and the processing head movement mechanism 55. The storage means 97 sequentially stores digital data obtained by converting image region data from the respective light-receiving regions 74$_1$ to 74$_n$ of the light-receiving element array 70 at a prescribed period, corresponding to the reaction containers 20$_1$ to 20$_n$ being the reaction spot array elements. The analysis means 98 analyzes the inspection through calculation based on the digital data stored in the storage means 97.

Subsequently, a lightguide aggregate inspection device 101 obtained by further embodying the lightguide aggregate inspection device 100 according to the second embodiment of the present invention that is illustrated in FIG. 7 will be described based on FIGS. 8(*a*) to 8(*c*) and 9.

As illustrated in FIGS. 8(*a*) to 8(*c*), a main portion of the lightguide aggregate inspection device 101 is incorporated into a casing having a function of a dark box, and an instruction from the user is performed to the device 101 using the operation panel 140 such as a touch-type tablet. The lightguide aggregate inspection device 101 broadly includes an accommodation unit group region 32 having the accommodation unit groups 32$_1$ to 32$_n$, a processing head 540 provided to be movable in the Y-axis direction with respect to the accommodation unit group region 32, and a processing head movement mechanism 55 that moves the processing head 540 in the Y-axis direction.

As illustrated in FIGS. 8(*a*) to 8(*c*) and 9, the accommodation unit group region 32 includes accommodation unit groups 32$_1$ to 32$_8$ (in the case of n=8 in FIG. 7) placed on a bottom 120*a* of the casing. The accommodation unit groups 32$_1$ to 32$_8$ include cartridge-like containers extending in the Y-axis direction and arrayed in multiple columns (in this example, 8 columns) in the X-axis direction. Each of the accommodation unit groups 32$_1$ to 32$_8$ includes a tip accommodation unit group 32*a*, a liquid accommodation unit group 32*b*, reaction containers 20$_1$ to 20$_8$, and a temperature raising and lowering body 8. In the tip accommodation unit groups 32*a*, attachment opening portions provided in wide tubes of the dispensing tips 46$_1$ to 46$_8$ each including a narrow tube and a wide tube are accommodated or can be accommodated so as to be on the upper side. In the liquid accommodation unit group 32*b*, various types of reagent solution such as specimen solution, magnetic particle suspension liquid, extraction solution, separation solution, cleaning liquid, PCR reagent, chemiluminescent substances, and trigger liquid serving as the prescribed reagent are accommodated. The liquid accommodation unit group 32*b* further includes a liquid accommodation unit in which temperature control can be performed. In the reaction containers 20$_1$ to 20$_8$, reaction related to inspection is performed. The reaction containers 20$_1$ to 20$_8$ correspond to the reaction spot array element, and serve as an array end liquid accommodation unit for measuring chemiluminescence, and in which temperature control can be performed. The temperature raising and lowering body 8 performs temperature rising and lowering of the reaction containers 20$_1$ to 20$_8$.

Furthermore, the accommodation unit group region 32 includes a light-receiving element array 700, lightguide paths 69$_1$ to 69$_8$, and a collective shutter mechanism 660. The light-receiving element array 700 includes a light-receiving surface 74 on which multiple light-receiving regions 74$_1$ to 74$_8$ are provided. The multiple light-receiving regions 74$_1$ to 74$_8$ each include at least one light-receiving element corresponding to each of the reaction containers 20$_1$ to 20$_8$ corresponding to the reaction spot array element, and receive light obtained based on an optical liquid state that can result from reaction in the reaction containers 20$_1$ to 20$_8$ being the reaction spot. The lightguide paths 69$_1$ to 69$_8$ respectively include multiple (in this example, 8) measurement ends 67$_1$ to 67$_8$ provided to be close to wall surfaces having translucency that serve as light guidable portions of the multiple (in this example, 8) reaction containers 20$_1$ to 20$_8$, and connection ends 68$_1$ to 68$_8$ provided to be close to the corresponding light-receiving regions 74$_1$ to 74$_8$ of the light-receiving surface 74. The collective shutter mechanism 660 brings the lightguide paths into a light-guiding state in a case in which the reaction containers 20$_1$ to 20$_8$ dispense prescribed trigger liquid using the dispensing tips 46$_1$ to 46$_8$, and brings the lightguide paths 69$_1$ to 69$_n$ into a light-shielding state in a case in which the dispensing to the liquid accommodation unit is not performed.

Herein, as the light-receiving element array 700, for example, as illustrated in FIGS. 8(*b*) and 8(*c*), a light-receiving element array (e.g., avalanche photodiode (APD) array manufactured by Hamamatsu Photonics) having 8 highly-sensitivity light-receiving elements arrayed on a substrate 740 provided in a dark box 700*a* is used. In this case, each of the light-receiving regions 74$_1$ to 74$_8$ only includes 1 light-receiving element, and light-receiving surfaces of the respective light-receiving elements correspond to the light-receiving regions 74$_1$ to 74$_8$. The connection ends of optical fibers of the lightguide paths 69$_1$ to 69$_8$ are provided to be in close contact or adhered so as to be in contact, or to be close to the light-receiving regions 74$_1$ to 74$_8$. In this case, as the digital data conversion unit 76, a pulse counter for counting the number of photons generated according to the amount of light received by the light-receiving element, through gate control that is based on a pulse signal generated at a prescribed period is used.

The prescribed period is defined by the measurement control unit 96 based on, for example, the types of luminescence and reagent that are used in the reaction containers 20$_1$ to 20$_8$, the mode of luminescence, and the like. A pulse signal having a corresponding period is generated and transmitted to the digital data conversion unit 76. In addition, in FIGS. 8(*a*) to 8(*c*) and 9, the drawing of partial lightguide paths $\mathbf{69}_2$ to $\mathbf{69}_8$ of the lightguide paths $\mathbf{69}_1$ to $\mathbf{69}_8$ is omitted, and visualization of the device is facilitated for descriptive purposes.

The reaction spot array elements are provided with a corresponding 1 of the reaction containers $\mathbf{20}_1$ to $\mathbf{20}_8$ as 1 reaction spot, and are arrayed in a line in the X-axis direction. Each of the reaction containers $\mathbf{20}_1$ to $\mathbf{20}_8$ corresponds to the reaction spot array element. In the present embodiment, unlike the first embodiment, no reaction spot array element is sealed in the dispensing tips $\mathbf{45}_1$ to $\mathbf{45}_8$.

The processing head 540 of the lightguide aggregate inspection device 101 includes a suction and discharge mechanism 430, a magnetic force mechanism 440, and a dispensing element Z-axis movement mechanism 420. The suction and discharge mechanism 430 performs suction and discharge of liquid with respect to the dispensing tips $\mathbf{46}_1$ to $\mathbf{46}_8$ being the dispensing elements. The magnetic force mechanism 440 can generate a magnetic force within the dispensing tips $\mathbf{46}_1$ to $\mathbf{46}_8$. The dispensing element Z-axis movement mechanism 420 can move the dispensing tips $\mathbf{46}_1$ to $\mathbf{46}_8$ in the Z-axis direction. A shutter driving member 451 is further included. The shutter driving member 451 drives the collective shutter mechanism 660 to bring the lightguide paths $\mathbf{69}_1$ to $\mathbf{69}_8$ into the light-guiding state in a prescribed time from when trigger liquid serving as the prescribed reagent is dispensed to the reaction containers $\mathbf{20}_1$ to $\mathbf{20}_8$, and to bring the lightguide paths $\mathbf{69}_1$ to $\mathbf{69}_8$ into the light-shielding state in other cases. The processing head movement mechanism 55 can be realized by providing, for example, a ball screw provided in the Y-axis direction, a motor for rotationally driving the ball screw, and a nut portion screwed with the ball screw, in the processing head 540. In addition, a reference sign 86 in FIG. 8(*a*) denotes a temperature raising and lowering body that performs temperature rising and lowering of other reaction containers 325 belonging to a reaction container group 32*c*.

Subsequently, the lightguide aggregate inspection device 101 will be further described in more detail based on FIGS. 8(*a*) to 10.

As illustrated in FIGS. 8(*a*) to 8(*c*) and 9, the collective shutter mechanism 660 includes 8 rods 66*a*, a light-shielding case 66*d*, and multiple (in this example, 8) optical fibers. The 8 rods 66*a* can concurrently move downward by lowering the shutter driving member 451, and are provided to be restorable to an original reference position by releasing the pressing of the driving member 451. The light-shielding case 66*d* shields light from the outside. The multiple optical fibers are provided to protrude from side plates of the light-shielding case 66*d*. The optical fibers form part of the lightguide paths $\mathbf{69}_1$ to $\mathbf{69}_8$.

In addition, in FIGS. 8(*a*) to 8(*c*), for facilitating visualization and for the descriptive purposes, the side plates of the light-shielding case 66*d* of the collective shutter mechanism 660 are illustrated in a removed state, the light-shielding case 66*d* internally has multiple (in this example, 8) compartments separated in the light-shielding state, and each compartment is provided with the rod 66*a*. In addition, a reference sign 66*c* denotes a retainer of an optical fiber provided on the removed side plate of the light-shielding case 66*d*. In each compartment within the light-shielding case 66*d*, each rod 66*a* is coupled to an opening and closing plate 66*b* formed of non-translucent member, and on which a shutter hole is provided. The opening and closing plate 66*b* is constantly biased upward by a spring (not illustrated) provided in each compartment, in such a manner as to move downward if the rods 66*a* are pressed, and to return to an original reference position if the pressing of the rods 66*a* is released.

The opening and closing plate 66*b* is provided with a shutter hole, and is constantly biased upward by the spring provided in each compartment, in the following manner. In a case in which the rods 66*a* are at a reference position, the opening and closing plate 66*b* brings a portion between rod lenses $\mathbf{670}_1$ to $\mathbf{670}_8$ (refer to FIG. 10) serving as the measurement ends and optical fibers, into the light-shielding state. By the pressing of the rods 66*a*, the opening and closing plate 66*b* moves downward, and the shutter hole is lowered to the position of the retainer 66*c*, so that the optical fibers and the reaction containers $\mathbf{20}_1$ to $\mathbf{20}_8$ enter the light-guiding state. By releasing the pressing of the rods 66*a*, the opening and closing plate 66*b* returns to an original reference position, so that the reaction containers $\mathbf{20}_1$ to $\mathbf{20}_8$ and the optical fibers enter the light-shielding state.

FIG. 10 illustrates the details of the accommodation unit group region 32. The opening and closing plate 66*b* is provided with a shutter hole. In a case in which the rods 66*a* are at a reference position, the opening and closing plate 66*b* brings a portion between the optical fibers and the rod lenses into the light-shielding state. By the pressing of the rods 66*a*, the opening and closing plate 66*b* lowers to a height position at which the optical fibers and the rod lenses $\mathbf{690}_1$ to $\mathbf{690}_8$ are provided, and brings a portion between the optical fibers and the rod lenses $\mathbf{690}_1$ to $\mathbf{690}_8$ into the light-guiding state.

As illustrated in FIG. 10, each of the accommodation unit groups $\mathbf{32}_1$ to $\mathbf{32}_8$ includes the tip accommodation unit group 32*a*, the liquid accommodation unit group 32*b*, and the reaction container group 32*c* corresponding to the reaction spot array element.

The tip accommodation unit group 32*a* includes 2 tip accommodation units 321 and 322 respectively accommodating 2 dispensing tips. The liquid accommodation unit group 32*b* includes a specimen solution accommodation unit 323, a liquid accommodation unit, and a liquid accommodation unit group 324. The liquid accommodation unit accommodates various types of reagents including magnetic particle suspension solution containing magnetic particles for extracting an objective substance to be inspected, from the specimen solution, cleaning liquid, separation liquid, and as chemiluminescent substances, for example, an acridinium labeled antibody, a trigger reagent (e.g., $H_2O_2$), NaOH solution, and the like. The liquid accommodation unit group 324 is provided for accommodating other reagents, and for mixing specimen solution and the reagent or the like. The reaction container group 32*c* includes the reaction container 325 and the reaction containers $\mathbf{20}_1$ to $\mathbf{20}_8$ for measurement.

As illustrated in FIG. 10, the liquid accommodation unit group region 32 is further provided with the reaction container 325, a temperature control block serving as a temperature raising and lowering body for performing temperature control of each of the reaction containers $\mathbf{20}_1$ to $\mathbf{20}_8$, and temperature controllers 85 and 86 including Peltier elements, fans, and fins. In addition, as denoted by reference signs A and B, connection portions of these rod lenses $\mathbf{670}_1$ to $\mathbf{670}_8$, optical fibers, and each unit are preferably shielded from light by rubber or the like.

Subsequently, the processing head 540 will be described in detail based on FIGS. 8(*a*) to 8(*c*) and 9.

The dispensing element Z-axis movement mechanism 420 provided in the processing head 540 includes a Y-axis movement frame 54*a*, a motor 47*a*, pulleys 47*b* and 47*d*, a ball screw 47*e*, and a Z-axis movement body 47*f*. The Y-axis movement frame 54*a* is connected to a nut portion provided in the Y-axis movement mechanism, and is movable in the Y-axis direction. The motor 47*a* is provided on the Y-axis movement frame 54*a*. The pulley 47*b* is connected with a rotational shaft of the motor 47*a*. The pulley 47*d* is connected with the pulley 47*b* via a timing belt 47*c*. The ball screw 47*e* is rotationally connected with the pulley 47*d*. The Z-axis movement body 47*f* is provided with a nut portion screwed with the ball screw 47*e*.

The processing head 540 includes the suction and discharge mechanism 430, and the suction and discharge mechanism 430 includes a motor 48*a* attached to the Z-axis movement body 47*f*, and a cylinder support member 48*b* to which multiple (in this example, 8) cylinders 48*d* are attached. Furthermore, a ball screw 48*g* extending in the Z-axis direction is pivotally supported on the Z-axis movement body 47*f*. The Z-axis movement body 47*f* is rotationally connected with a pulley 48*l* rotationally connected via a pulley 48*i* connected with a rotational shaft of the motor 48*a* and a timing chart 48*k*. Multiple (in this example, 8) dispensing tips $46_1$ to $46_8$ communicated with the cylinders 48*d* to be detachably attached to the leading ends of the cylinders 48*d* are provided. The suction and discharge mechanism 430 further includes 8 piston rods 48*c* sliding within the cylinders 48*d*, and a suction and discharge plate 48*h* engaged with the 8 piston rods 48*c*.

A nut portion is attached to the suction and discharge plate 48*h*, and is screwed with the ball screw 48*g*, to be vertically moved by the motor 48*a*. A tip detaching and attaching plate 48*e* is provided on the lower portion of the suction and discharge plate 48*h*, on the upper portion of the nozzles, and on the lower side of the cylinders 48*d*. The tip detaching and attaching plate 48*e* has an inner diameter larger than an outer diameter of the nozzles, but smaller than an outer diameter of the dispensing tips $46_1$ to $46_8$. On the tip detaching and attaching plate 48*e*, multiple (in this example, 8) holes for detaching and attaching provided so as to let the nozzles through are made. By driving the suction and discharge plate 48*h* to lower downward by a prescribed distance or more, the dispensing tips $46_1$ to $46_8$ are pressed via a detaching and attaching rod 48*j*, so as to be concurrently detachable from the nozzles. The lower end of the detaching and attaching rod 48*j* is attached to the tip detaching and attaching plate 48*e*. On the upper side thereof, the detaching and attaching rod 48*j* is supported with being elastically-biased upward by the cylinder support member 48*b*. The upper end thereof is at a position separated from the suction and discharge plate 48*h* by the prescribed distance.

As illustrated in FIG. 9, the tip detaching and attaching plate 48*e* is provided with a shutter driving member 451 protruding downward, on the lower side thereof. After moving the dispensing tips $46_1$ to $46_8$ of the processing head 540 to the position on the upper portion of the reaction containers $20_1$ to $20_8$ using the processing head movement mechanism 55 and the dispensing element Z-axis movement mechanism 420, by moving the Z-axis movement body 47*f* downward using the dispensing element Z-axis movement mechanism 420, the shutter driving member 451 is lowered and the 8 rods 66*a* are concurrently pressed. The lightguide paths $69_1$ to $69_8$ can be thereby brought into the light-guiding state using the collective shutter mechanism 660.

As illustrated in FIGS. 8(*a*) to 8(*c*) and 9, on the lower side of the Y-axis movement frame 54*a* of the processing head 540, a magnetic force mechanism support plate 54*b* is provided. On the lower side of the magnetic force mechanism support plate 54*b*, a magnetic force mechanism 440 is provided. In the magnetic force mechanism 440, multiple (in this example, 8) permanent magnets 44*a* are arrayed on a magnet array member 44*b* in the X-axis direction in a line at the same interval as the dispensing tips $46_1$ to $46_8$, and the magnet array member 44*b* is provided to be movable in the Y-axis direction close to and away from the dispensing tips $46_1$ to $46_8$ by an actuator 44*c*.

As illustrated in FIGS. 8(*b*) and 8(*c*), the light-receiving element array 700 is provided with a substrate 740 of a light-receiving element array covered by a dark box 700*a*. The connection ends of the lightguide paths $69_1$ to $69_8$ are arrayed on the substrate 740 in a grid, and the connection ends corresponding to the reaction containers $20_1$ to $20_8$ serving as the reaction spot array elements are provided to be in close contact with or adhered to the respective light-receiving regions $74_1$ to $74_8$.

Subsequently, an operation of the lightguide aggregate inspection device 101 according to the second embodiment will be described.

The description will be given of a case in which, by using acridinium ester derivative as a compound in a chemiluminescence method, an antigenic substance or antibody substance serving as an objective substance in serum is directly labeled, and is used as a tracer of immunoassay. In other words, detection of chemiluminescence is performed by the CLIA method.

In step S101, serum sample solution collected from 8 subjects is accommodated in the specimen solution accommodation unit 323, or the specimen solution accommodation unit 323 in which the collected serum sample solution is accommodated in advance is installed in a hole of a cartridge container.

In step S102, the nozzles of the processing head 540 are moved by the Y-axis movement mechanism to the tip accommodation unit 321 in the tip accommodation unit group 32*a*, and by lowering the Z-axis movement body 47*f* using the dispensing element Z-axis movement mechanism 420, the 8 dispensing tips $46_1$ to $46_8$ are attached to the nozzles. Using the dispensing tips $46_1$ to $46_8$, for example, 0.1 mL of serum solution is sucked from the specimen solution accommodation unit 323, and concurrently discharged into the reaction containers 325 within the reaction container group 32*c*.

In step S103, the processing head 540 is moved in the Y-axis direction, and by lowering the piston rods 48*c* by the prescribed distance or more by the motor 48*a* provided in the processing head 540, the dispensing tips $46_1$ to $46_8$ contaminated by specimen, i.e., the 8 dispensing tips are desorbed to an original position of the tip accommodation unit by the tip detaching and attaching plate 48*e* positioned on the upper portion of the nozzle. New dispensing tips $46_1$ to $46_8$ accommodated in a tip accommodation unit 322 of the tip accommodation unit group 32*a* are attached, the processing head 540 is moved in the Y-axis direction, and 0.1 mL of acridinium labeled antibody accommodated in any of the liquid accommodation unit group 32*b* is sucked and moved in the Y-axis direction to the 8 reaction containers 325 to be discharged, and is incubated for 120 minutes at room temperature.

In step S104, for inspecting the presence or absence of the antigenic substance in serum to be measured, by moving the processing head 540 in the Y-axis direction, the dispensing tips $46_1$ to $46_8$ attached to the nozzles are move to the upper portion of any of the liquid accommodation unit group 32*b* in which magnetic particle suspension liquid in which magnetic particles to which an antibody specifically-bondable to the antigenic substance is fixed on their surfaces are suspended is accommodated, are lowered using the dispensing element Z-axis movement mechanism 420, so that the leading ends of the dispensing tips 46$_1$ to 46$_8$ are inserted into the liquid accommodation unit, 0.5 mL of the accommodated magnetic particle suspension liquid is sucked into the dispensing tips 46$_1$ to 46$_8$, raised using the Z-axis movement mechanism 420, moved by the Y-axis movement mechanism to the reaction containers 325, lowered using the Z-axis movement mechanism 420, and the suspension liquid is discharged into the reaction containers 325 and agitated by repeating suction and discharge by vertically moving the piston rods 48*c* concurrently.

In step S105, by incubating the suspension liquid in the reaction container at room temperature for 30 minutes, an antigenic substance serving as an objective substance that is labeled by the acridinium labeled antibody in the specimen solution is bonded to the magnetic particles and fixed.

In step S106, the dispensing tips 46$_1$ to 46$_8$ are immobilized at a prescribed height position by the dispensing element Z-axis movement mechanism 420, suction and discharge is repeated by vertically moving the suction and discharge plate 48*h* in a state in which the dispensing tips 46$_1$ to 46$_8$ are concurrently moved close to the magnets 44*a* using the magnetic force mechanism 440, the processing head 540 is moved by the Y-axis movement mechanism with the dispensing tips 46$_1$ to 46$_8$ remaining close to the magnets 44*a*, and is positioned on the upper portion of the liquid accommodation unit in which cleaning liquid is accommodated, and the dispensing tips 46$_1$ to 46$_8$ are lowered using the dispensing element Z-axis movement mechanism 420 and cleaned by repeating suction and discharge in a state in which the magnets 44*a* are separated, so that B/F separation is performed.

In step S107, by moving the magnets 44*a* of the magnetic force mechanism 440 close to the dispensing tips 46$_1$ to 46$_8$ again, the magnets 44*a* are moved by the Y-axis movement mechanism to the reaction containers 20$_1$ to 20$_8$ of the reaction container group 32*c* in which, for example, 0.1 mL of pure water serving as separation liquid is accommodated, in the state being stuck to the inside wall, the dispensing tips 46$_1$ to 46$_8$ are inserted into the reaction containers 20$_1$ to 20$_8$ by the dispensing element Z-axis movement mechanism 420, and resuspended in the liquid in a state in which the magnets 44*a* are separated, the labeled objective substance is separated from magnetic particles, and the magnetic particles are removed.

In step S108, the dispensing tips 46$_1$ to 46$_8$ are moved in the Y-axis direction, 0.2 mL of $H_2O_2$ and 0.2 mL of NaOH that serve as trigger reagent are sucked and transferred to the upper portion of the reaction containers 20$_1$ to 20$_8$, by discharging the trigger liquid concurrently into the reaction containers 20$_1$ to 20$_8$ when the dispensing tips 46$_1$ to 46$_8$ are lowered in the Z-axis direction to a prescribed height by the dispensing element Z-axis movement mechanism 420, and simultaneously pressing the 8 rods 66*a* of the collective shutter mechanism 660 provided to be adjacent to the reaction containers 20$_1$ to 20$_8$, to a prescribed height by the shutter driving member 451, a portion between the rod lens and the optical fiber is brought into a light-guiding state by the collective shutter mechanism 660, and all of the light-guide paths 69$_1$ to 69$_8$ are brought into the light-guiding state, and accordingly, portions from the reaction containers 20$_1$ to 20$_8$ to the connection ends enter the light-guiding state, so that highly-sensitive light-receiving elements of the respective light-receiving regions 74$_1$ to 74$_8$ of the light-receiving element array 700 can receive light that is based on an optical state in the reaction containers 20$_1$ to 20$_8$.

In step S109, in a case in which there is an antigenic substance serving as an objective substance that is labeled by the acridinium labeled antibody, in the reaction container by the trigger liquid discharged from the dispensing tips 46$_1$ to 46$_8$, chemiluminescence is caused, and the light-receiving element array 700 receives light for a prescribed measurement time. Thus, based on the presence or absence of chemiluminescence, the presence or absence of an antigen in serum of each of the subjects is output at each prescribed period by converting the intensity or luminance of received light in the reaction container into corresponding digital data at each prescribed period, for each of the reaction containers, by the digital data conversion unit 76, stored into the storage means 97, and calculated and analyzed by the analysis means 98, so that a target biological substance can be inspected. In this case, the "prescribed period" is controlled by the measurement control unit 96 in such a manner that, for example, digital conversion is performed defined times (once or more, preferably multiple times) within a stable light receptible time of the luminescence or the like (alternatively, within the life of luminescence or the like, or within a specified time). In the case of receiving light multiple times at the prescribed period, the time dependence of luminance change can be analyzed by the analysis means based on obtained luminance data, a reaction speed and reactivity of a target biological substance can be obtained based on the rise time up to a peak value of a curve serving as a function of time that is drawn by the luminance and a speed, and a reaction amount of the target biological substance can be measured by a time integral value of the curve drawn by the luminance. In addition, the larger the number of times of light receiving, the more accurate analysis can be performed, but the number of times is restricted by luminescence life, and a time required for light receiving. For example, in a case in which the above-described instantaneous luminescence type chemiluminescence is used as a luminescence mode, if about 2 seconds, for example, are set as luminescence life leaving preceding and subsequent margins, and a light-receiving time (time required for photon counting, i.e., a digital data conversion time) is set to, for example, 2 msec as the prescribed period, light receiving and digital data conversion can be repeated about 1000 times concurrently for each reaction spot array element.

Each of the embodiments described above is given for specifically describing the present invention for better understanding, and does not limit other configurations. Thus, the embodiments can be modified without changing the gist of the invention. For example, in the above examples, the description has been given only of a case in which, in a reaction spot array, reaction spot array elements or reaction spots are arrayed so as to have translation symmetry in 2-axis directions and a 1-axis direction. Alternatively, reaction spot array elements or reaction spots may be arrayed in 3-axis directions or more.

In addition, in the above examples, the description has been given only of a case in which luminescence is performed as an optical state. In addition to this case, coloring and light variation can be performed by receiving light generated by coloring and light variation. In addition, a reagent of chemiluminescence is not limited to acridinium ester derivative, horseradish peroxidase, and the like that are described above.

In the above examples, the description has been given only of the case of combining with a processing head. Nevertheless, measurement can be performed without using the processing head. In addition, the devices described in the embodiments of the present invention, components forming these devices, or devices, reagents, and the like that form these components can be appropriately selected and appropriately changed to be combined with one another. For example, in a case in which inspection of a chemiluminescent substance, a reaction spot array, a reaction spot array element, a reaction spot, a light-receiving element array, a light-receiving element, a lightguide path, a digital data conversion unit, a dispensing element, a measurement control unit, or the like, or inspection in, for example, serum solution is performed, serum solution is condensed using magnetic particles, and an antibody corresponding to each particle is fixed and used, whereby the presence or absence of an antigen of each subject can be inspected.

In addition, in the subject application, spatial indications such as "X-axis", "Y-axis", "Z-axis", "upper portion", "lower portion", "inside", "outside", "vertical", "row", and "column" are provided only for describing the drawings, and do not limit to a specific spatial direction or arrangement of the structure.

Numerical values, the number of times, shapes, numbers, amounts, and the like that are used in the above description are not limited cases. For example, the description has been given only of a case in which the number of reaction spot array elements is 16 or 8, and the description has been given only of a case in which the number of reaction spots belonging to each reaction spot array element is 50 or 1. Needless to say, these numbers are not limited to these cases.

INDUSTRIAL APPLICABILITY

The present invention relates to a lightguide aggregate inspection device and a method of the same, and is for performing inspection of a specimen collected from a subject or the like, and optical measurement and analysis thereof, and is useful especially in a field that requires the handling of a biological macromolecule such as gene, immune system, amino acid, protein substance, and sugar, or a biological low molecular, and in, for example, various fields such as a biochemistry field, an industrial field, an agricultural field such as food, agriculture, and fishery processing, a pharmaceutical field, and a medical field such as sanitation, health, immunity, illness, and heredity.

REFERENCE SIGNS LIST

10, 11, 100, 101 lightguide aggregate inspection device
2, 20 reaction spot array
$\mathbf{2}_1, \ldots, \mathbf{2}_n$, $\mathbf{21}_1, \ldots, \mathbf{21}_{16}$ reaction spot array element
$\mathbf{20}_1, \ldots, \mathbf{20}_8$ reaction container (reaction spot array element)
22 reaction spot
3, 30, 31, 32 accommodation unit group region
$\mathbf{3}_1, \ldots, \mathbf{3}_n$, $\mathbf{31}_1, \ldots, \mathbf{31}_{16}$, $\mathbf{32}_1, \ldots, \mathbf{32}_8$ accommodation unit group
$\mathbf{4}_1, \ldots, \mathbf{4}_n$, $\mathbf{40}_1, \ldots, \mathbf{40}_n$, $\mathbf{41}_1, \ldots, \mathbf{41}_{16}$, $\mathbf{46}_1, \ldots, \mathbf{46}_8$ dispensing tip (dispensing element)
42, 420, 421 dispensing element Z-axis movement mechanism
43, 430, 431 suction and discharge mechanism
44, 440, 441 magnetic force mechanism
5, 51 array processing device
52, 54, 521, 540 processing head
53, 55 processing head movement mechanism
65, 651 measurement end Z-axis movement mechanism
$\mathbf{6}_1, \ldots, \mathbf{6}_n$, $\mathbf{60}_1, \ldots, \mathbf{60}_n$, $\mathbf{61}_1, \ldots, \mathbf{61}_{16}$, $\mathbf{69}_1, \ldots, \mathbf{69}_8$ lightguide path
$\mathbf{62}_1, \ldots, \mathbf{62}_{16}$, $\mathbf{67}_1, \ldots, \mathbf{67}_8$ measurement end
63, 631 measurement end support body
$\mathbf{64}_1, \ldots, \mathbf{64}_n$, $\mathbf{68}_1, \ldots, \mathbf{68}_n$ connection end
7, 70, 71, 700 light-receiving element array (CCD image sensor)
72, 721, 74 light-receiving surface
$\mathbf{72}_1, \ldots, \mathbf{72}_n$, $\mathbf{74}_1, \ldots, \mathbf{74}_n$ light-receiving region
75, 76 digital data conversion unit
8, 80, 81 temperature raising and lowering body
82 vertically movable body forward and backward drive mechanism
83, 84, 85, 86 temperature controller
9, 90 CPU+program+memory (information processing unit)
91, 95 extraction/reaction control unit
92, 96 measurement control unit
93, 97 storage means
94, 98 analysis means

The invention claimed is:

1. A lightguide aggregate inspection device comprising:
a reaction spot array including multiple reaction spot array elements having at least one reaction spot in which reaction related to inspection is performed, and which is provided at a predefined different position identifiable from an outside;
a light-receiving element array having a light-receiving surface provided with multiple light-receiving regions each having at least one light-receiving element corresponding to each of the reaction spot array elements, and receiving light obtained based on an optical state that can result from reaction in each of the reaction spots;
multiple lightguide paths provided to correspond to the reaction spot array elements, and each having a measurement end provided to be close to or in contact with, or to be movable close to or into contact with 1 of the reaction spots, and a connection end provided to be close to or in contact with the light-receiving region;
a digital data conversion unit configured to sequentially convert multiple image region data sequentially obtained, at a prescribed period, from the light-receiving elements corresponding to the light-receiving regions, into digital data to obtain multiple digital data for each of the light-receiving regions;
a storage means configured to sequentially store the digital data; and
an analysis means configured to analyze a temporal change in an optical state of each reaction spot array element, based on the digital data, and concurrently perforin inspection for each reaction spot array element.

2. The lightguide aggregate inspection device according to claim 1, wherein the reaction spot array element includes 2 or more reaction spots, and
wherein the lightguide aggregate inspection device further includes:
a measurement end support body configured to support a multiple of the measurement ends in an array set according to an array of the reaction spot array elements; and
a measurement end movement mechanism configured to make the measurement end support body relatively-movable with respect to the reaction spot array, and to thereby enable the measurement ends to concurrently move close to or into contact with the reaction spots corresponding to the respective reaction spot array elements.

3. The lightguide aggregate inspection device according to claim 2, wherein, in each of the reaction spot array elements, 2 or more reaction spots are arrayed so as to be congruent to each other, the reaction spot array elements are arrayed so as to have translation symmetry to each other, and the measurement end support body is arranged so as to enable the measurement ends provided to correspond to the respective reaction spot array elements, to concurrently and sequentially move close to or into contact with 2 or more of the reaction spots corresponding between the reaction spot array elements.

4. The lightguide aggregate inspection device according to claim 1, wherein, on a light-receiving surface of the light-receiving element array, the respective light-receiving regions provided to correspond to the reaction spot array elements are set in a grid at a prescribed interval according to an array of the reaction spot array elements.

5. The lightguide aggregate inspection device according to claim 1, wherein the reaction spot array or the reaction spot array element includes 1 or 2 or more inspection carriers in which predefined types of inspection substances related to the inspection are fixed in multiple different reaction spots at predefined positions identifiable from the outside.

6. The lightguide aggregate inspection device according to claim 1, wherein the reaction spot array element is provided with 1 reaction spot, the reaction spot is provided with 1liquid accommodation unit that can accommodate predefined types of solution related to the inspection, and each of the measurement ends is provided to be close to or in contact with a light guidable portion of the liquid accommodation unit.

7. The lightguide aggregate inspection device according to claim 1, further comprising a processing head provided with 2 or more dispensing elements that are provided to correspond to the respective reaction spot array elements, and can perform suction and discharge of liquid, wherein the dispensing elements are provided to be relatively movable with respect to an accommodation unit group in which multiple accommodation units provided to correspond to the respective reaction spot array elements are arrayed, leading ends of the dispensing elements are provided to be concurrently insertable into the respective liquid accommodation units of the accommodation unit group, and the dispensing elements perform suction and discharge of liquid accommodated in the respective liquid accommodation units, with respect to the reaction spot array elements.

8. The lightguide aggregate inspection device according to claim 7, wherein the reaction spot array element is an inspection carrier, and is sealed in the dispensing element, the dispensing element performs suction and discharge of liquid with respect to the inspection carrier, the inspection carrier is provided in such a manner that each fixed position is identifiable from the outside of the dispensing element, and the measurement end is provided to be movable while being close to or in contact with the dispensing element, according to an array of reaction spots, by being provided to be relatively movable with respect to the dispensing element by at least the measurement end movement mechanism.

9. The lightguide aggregate inspection device according to claim 1, further comprising a shutter mechanism configured, in a case in which a prescribed reagent moves into contact with or is dispensed to the reaction spot which the measurement end has moved close to or into contact with, or a portion accommodating the reaction spot, to bring the lightguide path connecting the measurement end and the connection end, into a light-guiding state, and in other cases, to bring the lightguide path into a light-shielding state.

10. A lightguide aggregate inspection method comprising:

a reaction step of performing reaction related to inspection in a reaction spot of a reaction spot array including multiple reaction spot array elements having the at least one reaction spot provided at a predefined different position identifiable from an outside;

a lightguide step of guiding light that is based on an optical state resulting from reaction in each of the reaction spots, through multiple lightguide paths corresponding to the respective reaction spot array elements and having measurement ends and connection ends that are provided to be movable close to or into contact with, or provided to be close to or in contact with respective reaction spots, to light-receiving regions of a light-receiving surface of a light-receiving element array, each of which has at least one light-receiving element and is provided to be close to or in contact with the connection end, corresponding to each of the reaction spot array elements;

a conversion step of sequentially converting image region data sequentially obtained, at a prescribed period, from the light-receiving elements corresponding to the light-receiving regions of the light-receiving element array, into digital data to obtain multiple digital data for each of the light-receiving regions;

a storage step of sequentially storing the converted digital data; and an analysis step of analyzing a temporal change in an optical state of each of the reaction spot array elements, based on the digital data, and concurrently performing inspection for each reaction spot array element.

11. The lightguide aggregate inspection method according to claim 10, wherein, in a case in which each of the reaction spot array elements includes 2 or more reaction spots, the lightguide step includes a measurement end moving step of concurrently moving the measurement ends close to or into contact with the corresponding reaction spots of the respective reaction spot array elements, by relatively moving a measurement end support body on which a multiple of the measurement ends are supported in an array set according to an array of the reaction spots, with respect to the reaction spot array.

12. The lightguide aggregate inspection method according to claim 10, wherein, in a case in which multiple reaction spot array elements in which 2 or more reaction spots are arrayed so as to be congruent to each other are arrayed so as to have translation symmetry to each other, the lightguide step guides light that is based on the optical state, to the light-receiving regions by moving, by the measurement end support body, the measurement ends provided to correspond to the respective spot array elements, in such a manner as to enable the measurement ends to concurrently and sequentially move close to or into contact with the corresponding 2 or more reaction spots provided in the corresponding reaction spot array elements.

13. The lightguide aggregate inspection method according to claim 10, wherein the reaction spot array element includes 1 inspection carrier in which predefined types of inspection substances related to the inspection are fixed in multiple different reaction spots at predefined positions identifiable from the outside, and the reaction step performs reaction related to inspection, by dispensing solution to the inspection carrier.

14. The lightguide aggregate inspection method according to claim 13, wherein the reaction spot array elements are sealed in 2 or more dispensing elements which have translucency and can perform suction and discharge of liquid, the dispensing elements are provided to be relatively movable with respect to an accommodation unit group in which liquid accommodation units are arrayed, leading ends of the dispensing elements are provided to be concurrently insertable into the respective liquid accommodation units of the accommodation unit group, and the reaction step performs reaction related to inspection with respect to the reaction spot array elements, by concurrently inserting the dispensing elements into the respective liquid accommodation units to perform suction and discharge of liquid accommodated in the liquid accommodation units.

15. The lightguide aggregate inspection method according to claim 10, wherein 1 reaction spot in the reaction spot array element is provided with 1 liquid accommodation unit that can accommodate predefined types of solution related to the inspection, and the lightguide step guides light that is based on an optical state, and the optical state in each of the reaction spots, from measurement ends provided to be close to or in contact with light guidable portions of the respective liquid accommodation units, to the light-receiving region having at least one light-receiving element provided to correspond to each of the reaction spots, through connection ends of multiple lightguide paths.

16. The lightguide aggregate inspection method according to claim 10, wherein the lightguide step includes a step of bringing a lightguide path connecting the measurement end and the connection end, into a light-guiding state, in a case in which a prescribed reagent contacts the reaction spot which the measurement end has moved close to or into contact with, or a prescribed reagent is dispensed to a portion accommodating the reaction spot, and bringing the lightguide path into a light-shielding state in other cases.

* * * * *

UNITED STATES PATENT AND TRADEMARK OFFICE

CERTIFICATE OF CORRECTION

PATENT NO. : 10,139,348 B2
APPLICATION NO. : 15/127119
DATED : November 27, 2018
INVENTOR(S) : Hideji Tajima It is certified that error appears in the above-identified patent and that said Letters Patent is hereby corrected as shown below:

In the Claims

In Claim 1, Column 36, Line 46, change "perforin inspection" to -- perform inspection --.

Signed and Sealed this
Nineteenth Day of February, 2019

Andrei Iancu
*Director of the United States Patent and Trademark Office*